United States Patent
Savage et al.

(10) Patent No.: US 11,739,116 B2
(45) Date of Patent: *Aug. 29, 2023

(54) METHODS FOR TREATING INFLAMMATION, AUTOIMMUNE DISORDERS AND PAIN

(71) Applicants: Paul B. Savage, Mapleton, UT (US); Carl Genberg, Las Vegas, NV (US)

(72) Inventors: Paul B. Savage, Mapleton, UT (US); Carl Genberg, Las Vegas, NV (US)

(73) Assignee: Brigham Young University, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/208,082

(22) Filed: Mar. 13, 2014

(65) Prior Publication Data

US 2014/0274913 A1    Sep. 18, 2014

Related U.S. Application Data

(60) Provisional application No. 61/794,721, filed on Mar. 15, 2013.

(51) Int. Cl.
| | |
|---|---|
| *C07J 41/00* | (2006.01) |
| *A61K 47/10* | (2017.01) |
| *A61K 47/42* | (2017.01) |
| *A61K 31/575* | (2006.01) |
| *A61K 45/06* | (2006.01) |
| *A61K 47/69* | (2017.01) |
| *A61K 47/64* | (2017.01) |
| *A61K 47/60* | (2017.01) |

(52) U.S. Cl.
CPC ......... *C07J 41/0088* (2013.01); *A61K 31/575* (2013.01); *A61K 45/06* (2013.01); *A61K 47/60* (2017.08); *A61K 47/643* (2017.08); *A61K 47/6921* (2017.08)

(58) Field of Classification Search
CPC .. A61K 31/56; A61K 2300/00; A61K 31/575; A61K 45/06; A61K 31/427; A61K 31/496; A61K 31/7036; A61K 31/7048; A61K 31/7052; A61K 38/06; A61K 38/12; A61K 38/14; A61K 47/60; A61K 47/643; A61K 47/6921; A61K 9/0078; C07J 41/0088; C07J 41/0055; A61P 11/00; A61P 11/02; A61P 19/08; A61P 1/00; A61P 1/02; A61P 1/04; A61P 25/04; A61P 27/16; A61P 29/00; A61P 31/04; A61P 37/00; A61P 37/06
USPC ...................................................... 514/169
See application file for complete search history.

(56) References Cited

U.S. PATENT DOCUMENTS

| | | |
|---|---|---|
| 821,187 A | 5/1906 | Peters |
| 3,843,779 A | 10/1974 | Norfleet |
| 4,248,236 A | 2/1981 | Linder et al. |
| 4,284,236 A | 8/1981 | Bradshaw |
| 4,289,755 A | 9/1981 | Dhabhar |
| 4,296,206 A | 10/1981 | Simons |
| 4,473,988 A | 10/1984 | Scott |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,865,855 A | 9/1989 | Hansen et al. |
| 4,972,848 A | 11/1990 | DiDomenico |
| 5,025,754 A | 6/1991 | Plyler |
| 5,286,479 A * | 2/1994 | Garlich .................... A61K 8/19 424/49 |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |

(Continued)

FOREIGN PATENT DOCUMENTS

| | | |
|---|---|---|
| CA | 2322847 A1 | 9/1999 |
| CA | 2640584 A1 | 8/2007 |

(Continued)

OTHER PUBLICATIONS

Bucki et al. (J. of Antimicrobial Chemotherapy (2007) 60, 535-545, 892).*

(Continued)

*Primary Examiner* — Dominic Lazaro

(74) *Attorney, Agent, or Firm* — Workman Nydegger

(57) ABSTRACT

Compositions and methods for treating, reducing, or preventing a disease or symptom such as gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain. The method includes identifying a patient in need of treatment and administering a therapeutically effective amount of at least one cationic steroid antimicrobial (CSA), or a pharmaceutically acceptable salt thereof. Kits comprising such compositions and instructions on such methods are also contemplated herein.

29 Claims, No Drawings

(56) References Cited

U.S. PATENT DOCUMENTS

| | | | |
|---|---|---|---|
| 5,763,430 | A | 6/1998 | Zasloff |
| 5,919,183 | A | 7/1999 | Field |
| 6,117,332 | A | 9/2000 | Hatch et al. |
| 6,143,738 | A | 11/2000 | Zasloff |
| 6,217,896 | B1 | 4/2001 | Benjamin |
| 6,224,622 | B1 | 5/2001 | Kotzev |
| 6,228,393 | B1 | 5/2001 | DiCosmo et al. |
| 6,329,488 | B1 | 12/2001 | Terry et al. |
| 6,344,184 | B1 | 2/2002 | Rolla |
| 6,350,738 | B1 * | 2/2002 | Savage ............... C07J 41/0055 514/182 |
| 6,486,148 | B2 * | 11/2002 | Savage ............... C07J 41/0055 514/169 |
| 6,562,318 | B1 | 5/2003 | Filler |
| 6,582,713 | B2 | 6/2003 | Newell et al. |
| 6,673,771 | B1 | 1/2004 | Greene et al. |
| 6,767,904 | B2 * | 7/2004 | Savage ............... C07J 41/0055 514/182 |
| 6,803,030 | B2 | 10/2004 | De Haen et al. |
| 6,803,066 | B2 | 10/2004 | Traeder |
| 6,824,044 | B1 | 11/2004 | Lapstun et al. |
| 6,872,303 | B2 | 3/2005 | Knapp et al. |
| 6,872,306 | B2 | 3/2005 | Shen |
| 6,939,376 | B2 | 9/2005 | Shulze et al. |
| 7,226,577 | B2 | 6/2007 | Cappelletti et al. |
| 7,235,552 | B1 | 6/2007 | Hesse et al. |
| 7,282,214 | B2 | 10/2007 | Wilcox et al. |
| 7,381,439 | B2 | 6/2008 | Hilgren et al. |
| 7,481,973 | B2 | 1/2009 | Beilfuss et al. |
| 7,598,234 | B2 * | 10/2009 | Savage ............... C07J 41/0055 514/182 |
| 7,611,692 | B2 | 11/2009 | Cappelletti et al. |
| 7,659,061 | B2 | 2/2010 | Hendl et al. |
| 7,754,705 | B2 * | 7/2010 | Savage ................. A61K 31/56 514/169 |
| 7,850,947 | B2 | 12/2010 | Cappelletti et al. |
| 7,854,941 | B2 | 12/2010 | Urban et al. |
| 7,993,903 | B2 | 8/2011 | Hayakawa et al. |
| 7,999,390 | B2 | 8/2011 | Ishigaki et al. |
| 8,211,879 | B2 | 7/2012 | Savage et al. |
| 8,420,050 | B2 | 4/2013 | Cappelletti et al. |
| 8,444,954 | B2 | 5/2013 | Cappelletti et al. |
| 8,529,681 | B1 | 9/2013 | Hibbs et al. |
| 8,530,002 | B1 | 9/2013 | Hibbs et al. |
| 8,557,031 | B1 | 10/2013 | Hibbs et al. |
| 8,623,416 | B2 | 1/2014 | Zasloff et al. |
| 8,691,252 | B2 | 4/2014 | Savage |
| 8,784,857 | B2 | 7/2014 | Savage |
| 8,787,857 | B2 | 7/2014 | Savage |
| 9,180,132 | B2 | 11/2015 | Fein et al. |
| 9,434,759 | B1 | 9/2016 | Savage |
| 9,527,883 | B2 | 12/2016 | Savage et al. |
| 9,533,063 | B1 | 1/2017 | Savage |
| 10,226,550 | B2 | 3/2019 | Savage et al. |
| 10,441,595 | B2 | 10/2019 | Genberg et al. |
| 10,568,893 | B2 * | 2/2020 | Savage ................... A61K 45/06 |
| 2002/0019376 | A1 * | 2/2002 | Savage ............... C07J 41/0055 514/169 |
| 2002/0091278 | A1 * | 7/2002 | Savage ............... C07J 41/0055 552/9 |
| 2002/0091433 | A1 | 7/2002 | Ding et al. |
| 2002/0115121 | A1 | 8/2002 | Garwin |
| 2003/0018306 | A1 | 1/2003 | Bucay-Couto et al. |
| 2003/0099717 | A1 | 5/2003 | Cabrera |
| 2003/0170354 | A1 | 9/2003 | Beelman et al. |
| 2003/0232791 | A1 | 12/2003 | Levitt et al. |
| 2004/0009227 | A1 | 1/2004 | Yao |
| 2004/0011358 | A1 | 1/2004 | Smaldone et al. |
| 2004/0018154 | A1 | 1/2004 | Pan |
| 2004/0058974 | A1 | 3/2004 | Courtney et al. |
| 2004/0071781 | A1 | 4/2004 | Chattopadhyay et al. |
| 2004/0126409 | A1 | 7/2004 | Wilcox et al. |
| 2004/0134292 | A1 | 7/2004 | Roth |
| 2004/0170563 | A1 | 9/2004 | Meade |
| 2004/0259445 | A1 | 12/2004 | Hilfenhaus et al. |
| 2005/0032765 | A1 | 2/2005 | Savage et al. |
| 2005/0075321 | A1 | 4/2005 | Ahlem et al. |
| 2005/0244468 | A1 | 11/2005 | Huang et al. |
| 2005/0267051 | A1 | 12/2005 | Lee et al. |
| 2006/0014738 | A1 | 1/2006 | Wachendorff-neumann et al. |
| 2006/0062742 | A1 | 3/2006 | Davis et al. |
| 2006/0269485 | A1 | 11/2006 | Friedman et al. |
| 2007/0053788 | A1 | 3/2007 | Zhao |
| 2007/0077292 | A1 | 4/2007 | Pinsky |
| 2007/0106393 | A1 | 5/2007 | Miles et al. |
| 2007/0134292 | A1 | 6/2007 | Suokas et al. |
| 2007/0170563 | A1 | 7/2007 | Chen |
| 2007/0190066 | A1 | 8/2007 | Savage et al. |
| 2007/0190067 | A1 | 8/2007 | Savage et al. |
| 2007/0190558 | A1 | 8/2007 | Savage et al. |
| 2007/0243225 | A1 | 10/2007 | McKay |
| 2007/0269375 | A1 | 11/2007 | Chen et al. |
| 2008/0085949 | A1 | 4/2008 | McGhee |
| 2008/0124376 | A1 | 5/2008 | Pruitt et al. |
| 2008/0174035 | A1 | 7/2008 | Winterton |
| 2008/0188819 | A1 | 8/2008 | Kloke et al. |
| 2008/0279944 | A1 | 11/2008 | Sawhney |
| 2009/0016973 | A1 | 1/2009 | Ratcliff et al. |
| 2009/0024101 | A1 | 1/2009 | Toshishige et al. |
| 2009/0054295 | A1 | 2/2009 | Vicari et al. |
| 2009/0068122 | A1 | 3/2009 | Pilch et al. |
| 2009/0099531 | A1 | 4/2009 | Griesbach, III |
| 2009/0124591 | A1 | 5/2009 | Diamond et al. |
| 2009/0226884 | A1 | 9/2009 | Tsujimoto et al. |
| 2009/0252781 | A1 | 10/2009 | Sawhney et al. |
| 2009/0279944 | A1 | 11/2009 | Schmitz et al. |
| 2009/0324517 | A1 | 12/2009 | Kline |
| 2010/0022681 | A1 | 1/2010 | Wang et al. |
| 2010/0092398 | A1 | 4/2010 | Reynolds |
| 2010/0226884 | A1 | 9/2010 | Chang et al. |
| 2010/0310478 | A1 | 12/2010 | Fitzgerald et al. |
| 2010/0330086 | A1 | 12/2010 | Savage et al. |
| 2011/0033540 | A1 | 2/2011 | Daniloff et al. |
| 2011/0071099 | A1 | 3/2011 | Bielawska et al. |
| 2011/0091376 | A1 | 4/2011 | Savage |
| 2011/0123624 | A1 | 5/2011 | Zasloff |
| 2011/0135742 | A1 | 6/2011 | Kim et al. |
| 2011/0171144 | A1 | 7/2011 | Wang et al. |
| 2011/0230589 | A1 | 9/2011 | Maggio et al. |
| 2012/0088733 | A1 | 4/2012 | Kim et al. |
| 2012/0107382 | A1 | 5/2012 | Savage et al. |
| 2012/0128793 | A1 | 5/2012 | Miller et al. |
| 2013/0004586 | A1 | 1/2013 | Vachon |
| 2013/0022651 | A1 | 1/2013 | Savage |
| 2013/0034500 | A1 | 2/2013 | Savage et al. |
| 2013/0040265 | A1 | 2/2013 | Park et al. |
| 2013/0053507 | A1 | 2/2013 | Savage |
| 2013/0089580 | A1 | 4/2013 | Boutros |
| 2013/0137668 | A1 | 5/2013 | Fein et al. |
| 2013/0234842 | A1 | 9/2013 | Genberg et al. |
| 2013/0236619 | A1 | 9/2013 | Savage |
| 2013/0243823 | A1 | 9/2013 | Genberg et al. |
| 2013/0243840 | A1 | 9/2013 | Savage et al. |
| 2013/0243842 | A1 | 9/2013 | Genberg et al. |
| 2013/0245760 | A1 | 9/2013 | Savage et al. |
| 2013/0280312 | A1 | 10/2013 | De Szalay |
| 2013/0280391 | A1 | 10/2013 | Savage |
| 2014/0062960 | A1 | 3/2014 | Kim et al. |
| 2014/0107090 | A1 | 4/2014 | Beus et al. |
| 2014/0194401 | A1 | 7/2014 | Genberg et al. |
| 2014/0219914 | A1 | 8/2014 | Govindan et al. |
| 2014/0271761 | A1 | 9/2014 | Savage et al. |
| 2014/0274913 | A1 | 9/2014 | Savage et al. |
| 2014/0305461 | A1 | 10/2014 | Pimenta et al. |
| 2014/0315873 | A1 | 10/2014 | Beus et al. |
| 2014/0336131 | A1 | 11/2014 | Savage et al. |
| 2014/0363780 | A1 | 12/2014 | Vazquez et al. |
| 2014/0369941 | A1 | 12/2014 | Vazquez et al. |
| 2015/0093423 | A1 | 4/2015 | Savage et al. |
| 2015/0110767 | A1 | 4/2015 | Savage et al. |
| 2015/0140063 | A1 | 5/2015 | Savage |
| 2015/0203257 | A1 | 7/2015 | Canegallo |
| 2015/0203527 | A1 | 7/2015 | Savage |

(56) References Cited

U.S. PATENT DOCUMENTS

| | | | |
|---|---|---|---|
| 2015/0239928 A1 | 8/2015 | Savage | |
| 2015/0258121 A1 | 9/2015 | Darien et al. | |
| 2015/0258122 A1 | 9/2015 | Beus et al. | |
| 2015/0258123 A1 | 9/2015 | Savage et al. | |
| 2015/0314342 A1 | 11/2015 | Beus et al. | |
| 2015/0366880 A1 | 12/2015 | Genberg et al. | |
| 2015/0374719 A1 | 12/2015 | Genberg et al. | |
| 2015/0374720 A1 | 12/2015 | Genberg et al. | |
| 2016/0022702 A1* | 1/2016 | Savage | A61K 45/06 514/3.1 |
| 2016/0045421 A1 | 2/2016 | Vazquez et al. | |
| 2016/0052959 A1 | 2/2016 | Savage | |
| 2016/0096864 A1 | 4/2016 | Savage | |
| 2016/0193232 A1 | 7/2016 | Beus et al. | |
| 2016/0199390 A1 | 7/2016 | Beus et al. | |
| 2016/0311850 A1 | 10/2016 | Savage et al. | |
| 2016/0311851 A1 | 10/2016 | Savage et al. | |
| 2017/0035677 A1 | 2/2017 | Vazquez et al. | |
| 2017/0080128 A1 | 3/2017 | Genberg et al. | |
| 2017/0137459 A1 | 5/2017 | Savage | |
| 2017/0210776 A1 | 7/2017 | Savage | |
| 2017/0232004 A1 | 8/2017 | Savage et al. | |
| 2017/0258963 A1 | 9/2017 | Savage et al. | |
| 2018/0164221 A1 | 6/2018 | Singh et al. | |
| 2018/0280550 A1 | 10/2018 | Savage | |
| 2019/0076581 A1 | 3/2019 | Savage et al. | |

FOREIGN PATENT DOCUMENTS

| | | |
|---|---|---|
| CA | 2842460 A1 | 1/2013 |
| CA | 2848567 A1 | 3/2013 |
| CA | 2888259 A1 | 4/2014 |
| CA | 2741177 C | 3/2018 |
| CN | 1236322 A | 11/1999 |
| CN | 101247838 A | 8/2008 |
| CN | 101378761 | 3/2009 |
| CN | 102145005 | 8/2011 |
| CN | 102172356 | 9/2011 |
| CN | 104039369 A | 9/2014 |
| DE | 1037074 | 8/1958 |
| EP | 0341951 | 11/1989 |
| EP | 1208844 | 5/2002 |
| EP | 1219631 | 7/2002 |
| EP | 0832094 B1 | 2/2004 |
| EP | 1058552 B1 | 6/2004 |
| EP | 1311531 B1 | 5/2016 |
| JP | 60-080457 A | 5/1985 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002-515019 A | 5/2002 |
| JP | 2002255771 | 9/2002 |
| JP | 2002534532 | 10/2002 |
| JP | 2002538093 | 11/2002 |
| JP | 2004-506599 A | 3/2004 |
| JP | 2004506645 | 3/2004 |
| JP | 2009-131625 A | 6/2009 |
| JP | 2010-059194 A | 3/2010 |
| JP | 2010533051 | 10/2010 |
| JP | 2010538074 | 12/2010 |
| JP | 2011527702 | 11/2011 |
| JP | 2014500741 | 1/2014 |
| JP | 2014-520900 A | 8/2014 |
| JP | 2014-530191 A | 11/2014 |
| JP | 2017-519036 A | 7/2017 |
| WO | WO 1995024415 | 9/1995 |
| WO | 98/05337 A1 | 2/1998 |
| WO | WO9827106 | 6/1998 |
| WO | 99/45024 A1 | 9/1999 |
| WO | WO 1999044616 | 9/1999 |
| WO | 00/35375 A1 | 6/2000 |
| WO | WO 2000042058 | 7/2000 |
| WO | WO 2002014342 | 2/2002 |
| WO | WO2002067979 | 9/2002 |
| WO | WO 2003015757 | 2/2003 |
| WO | 03/66119 | 8/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | 2008/048340 A2 | 4/2008 |
| WO | WO2008096149 | 8/2008 |
| WO | 2009049370 | 4/2009 |
| WO | WO 2008038965 | 4/2009 |
| WO | WO 2009079066 | 6/2009 |
| WO | WO 2009/144708 A | 12/2009 |
| WO | WO2009144708 | 12/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | 2013/013221 A1 | 1/2013 |
| WO | 2013/013223 A1 | 1/2013 |
| WO | WO 2013029055 | 2/2013 |
| WO | WO 2013029059 | 2/2013 |
| WO | 2013/040265 A1 | 3/2013 |
| WO | WO2013131060 | 6/2013 |
| WO | WO2013/109236 | 7/2013 |
| WO | 2013/163359 A1 | 10/2013 |
| WO | 2013167743 | 11/2013 |
| WO | 2014062960 | 4/2014 |
| WO | 2014/107740 A2 | 7/2014 |
| WO | WO 2014151411 | 9/2014 |
| WO | WO2015058087 | 4/2015 |
| WO | 2015/138716 A2 | 9/2015 |
| WO | WO2015200815 | 12/2015 |
| WO | WO2016172543 | 10/2016 |
| WO | 2016186821 | 11/2016 |
| WO | 2017/053355 A1 | 3/2017 |

OTHER PUBLICATIONS

Munoz-Juarez et al. (Dis Colon Rectum 2001;44: No. 1, 20-26).*
Yanshu Feng (Theses Brigham Young University, BYU Scholars Archive, dated Dec. 19, 2011, 892).*
Gregory M. Barton (Journal of Clinical Investigation, vol. 118, No. 2, Feb. 2008, Review Series, pp. 413-420).*
Chen et al. (J Drug Target. Dec. 2012; 20(10):856-63).*
Dumortier, G et al. (Pharmaceutical Research, vol. 23, No. 12, Dec. 2006).*
Lawrence, Toby (The Nuclear Factor NF-?B Pathway in Inflammation, Cold Spring Harb Perspect Biol. Dec. 2009; 1(6): a001651).*
Dumortier G, (A review of poloxamer 407 pharmaceutical and pharmacological characteristics. Pharm Res. Dec. 2006;23(12):2709-28. doi: 10.1007/s11095-006-9104-4. Epub Nov. 11, 2006. PMID: 17096184.).*
U.S. Appl. No. 14/694,028, filed Apr. 23, 2015, Beus et al.
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 2004.
International Search Report for PCT Application No. PCT/US2014/034986 dated Aug. 28, 2014.

(56) References Cited

OTHER PUBLICATIONS

International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Zanger et al., "Structure-Activity Relationship and Drug Design", Remington's Pharmaceutical Sciences, Chapter 27, 16th Edition, 1980, pp. 420-425.
U.S. Appl. No. 13/783,007, filed Mar. 1, 2013, Savage.
U.S. Appl. No. 14/288,126, filed May 27, 2014, Savage et al.
U.S. Appl. No. 14/339,342, filed Jul. 23, 2014, Vasquez et al.
U.S. Appl. No. 14/341,304, filed Jul. 25, 2014, Savage et al.
U.S. Appl. No. 14/364,283, filed Jul. 29, 2014, Vasquez et al.
U.S. Appl. No. 14/398,094, filed Oct. 30, 2014, Savage et al.
U.S. Appl. No. 14/515,858, filed Oct. 16, 2014, Savage et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl file/ol0062704 sl.pdf.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/0475485 dated Feb. 17, 2010.
International Search Report for PCT Application No. PCT/US2011/059225 dated Jan. 31, 2012.
International Search Report for PCT Application No. PCT/US2012/047750, dated Oct. 15, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/000,010, filed Dec. 17, 2012, Restriction Requirement dated Dec. 4, 2012.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.
U.S. Appl. No. 13/554,930, filed Jul. 20, 2012, Office Action dated Jul. 11, 2014.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.

(56) References Cited

OTHER PUBLICATIONS

U.S. Appl. No. 13/783,131, filed Mar. 1, 2013, Office Action dated Oct. 23, 2014.
U.S. Appl. No. 14/056,122, filed Oct. 17, 2013, Office Action dated Sep. 3, 2014.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
U.S. Appl. No 13/615,244, filed Sep. 13, 2012, Office Action dated Jan. 16, 2015.
U.S. Appl. No 14/257,776, filed Apr. 21, 2014, Restriction Requirement dated Jan. 22, 2015.
U.S. Appl. No 14/364,283, filed Jul. 29, 2014, Office Action dated Feb. 11, 2015.
U.S. Appl. No 14/339,342, filed Jul. 23, 2014, Office Action dated Mar. 5, 2015.
U.S. Appl. No 13/554,930, filed Jul. 20, 2012, Final Office Action dated Mar. 16, 2015.
U.S. Appl. No 13/783,007, filed Mar. 1, 2013, Restriction Requirement dated Mar. 31, 2015.
U.S. Appl. No 13/000,010, filed Dec. 17, 2010, Office Action dated Apr. 14, 2015.
U.S. Appl. No 14/257,776, filed Apr. 21, 2014, Office Action dated Apr. 16, 2015.
BASF, Pluronic® Block Copolymer NF Grades (Poloxamer NF Grades), Technical Bulletive (2004).
Bush, "Staphylococcal Infections", Merck Manuals Professional Edition, http://www.merckmanuals.com/professional/infectious-diseases/gram-positive-cocci/staphylococcal-infections.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-576, 1954.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
U.S. Appl. No. 14/873,013, filed Oct. 10, 2015, Office Action dated Jul. 3, 2017.
U.S. Appl. No. 14/341,304, filed Jul. 25, 2014, Office Action dated Jul. 14, 2017.
U.S. Appl. No. 15/934,534, filed Mar. 23, 2018, Savage.
U.S. Appl. No. 15/895,848, filed Feb. 13, 2018, Genberg, et al.
U.S. Appl. No. 15/926,534, filed Mar. 20, 2018, Savage.
U.S. Appl. No. 15/926,577, filed Mar. 20, 2018, Savage et al.
Belikov V.G., Pharmaceutical Chemistry, M., Higher School, 1993, p. 43-47.
Food definition, Merriam Webster, https://www.merriam-webster.com/dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.
U.S. Appl. No. 14/873,013, Jan. 13, 2017, Final Office Action cited in U.S. Appl. No. 14/873,013 dated Jan. 13, 2017.
U.S. Appl. No. 14/341,304, Feb. 21, 2017, Final Office Action cited in U.S. Appl. No. 14/431,304 dated Feb. 21, 2017.
U.S. Appl. No. 14/341,304, Feb. 28, 2018, Office Action cited in U.S. Appl. No. 14/341,304 dated Feb. 28, 2018.
U.S. Appl. No. 14/873,013, Mar. 29, 2018, Office Action cited in U.S. Appl. No. 14/873,013 dated Mar. 29, 2018.
U.S. Appl. No. 16/842,211, filed Nov. 8, 2018, Savage.
Weijian Ye et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/i.bioorg.2013.08.003.
"Quaternary Ammoniuim Compounds", Van Nostrand's Scientific Encyclopedia, Jan. 1, 2006, John Wiley & Sons, Inc.
Opsenica D, et al., "Cholic Acid Derivatives as 1,2,4,5-Tetraoxane Carriers: Structure and Antimalarial and Antiproliferative Activity", J. Med Chem. Aug. 2000.
Valkonen, et al., "Bile acid amidoalcohols: simgle organogelators", Biosens Bioelectron, Dec. 2004.
Deepak B. Salunke et al., "Amino Functionalized Novel Cholic Acid Derivatives Induce HIV-1 Reglication and Syncytia Formation in T Cells", J. Med. Chem. 2006.
Ding, et al., "Correlation of the Antibacerial Activities of Cationic Peptid Antibiotics and Cationic Steroid Antibiotics", J. Med. Chem., vo. 45, pp. 663-669 (Year: 2002).
Kuroda, et al., "Ceragenin CSA-13 induces cell cycle arrest and antiproliferative effects in wild-type and p52 null mutant HCT116 colon cancer cells", Preclinical Report, Wolters Kluwer Health 2013.
Dennison et al., "Anticancer a-Helical Peptides and Structure/Function Relationships Underpinning their Interactions with Tumour Cell Membranes", Current Protein and Peptide Science, 2006, 7, No. 6, pp. 1-13.
Ding, et al., "Origins of cell selectivity of cationic steroid antibiotics", Journal of American Chemical Society, Oct. 2004, pp. 13642-13648.
International Search Report and Written Opinion received for PCT Patent Application No. PCT/US2020/034297, dated Aug. 26, 2020, 8 pages.
Papo et al., "Host defense peptides as new weapons in cancer treatment", Cmls Cellular And Molecular Life Sciences, vol. 62, No. 7-8, Apr. 1, 2005, pp. 784-790.

(56) References Cited

OTHER PUBLICATIONS

International Search Report for PCT Application No. PCT/US2018/023566 dated Mar. 21, 2018.
Uncategorized: CSA Biotechnologies LLC, Apr. 5, 2011.
"Martindale: the complete drug reference, Cetrimide; Cetylpyridinium chloride Ed-Parfitt K", Jan. 1, 2000, pp. 1105-1106.
Barton, Journal of Clinical Investigation, vol. 118, No. 2, Feb. 2008, Review Series, pp. 413-420.
Feng, Theses Brigham Young University, BYU Scholars Archive, dated Dec. 19, 2011, 892.
Chen et al, J Drug Target, Dec. 2012; 20(10):856-63, 892.
Ogata et al. Intramammary application of ozone therapy to acute clinical mastitis in dairy cows. J. Vet. Med. Sci. 62(7): 681-686, 2000.
De Haas et al. Associations between pathogen-specific cases of clinical mastitis and somatic cell count patterns. J. Dairy Sci. 87: 95-105.
"mouth rinse" definition by Medical dictionay. Retrieved from http://medical-dictionary.thefreedictionary.com/mouth-i-rinse.
Ahmed, Hydrogel: Preparation, characterization, and applications: A review, Journal of Advanced Research (2015) 6:105-121 (Year: 2015).
BASF, [Retrieved from internet <URL: https://worldaccount.basf.com/wa/NAFTA.about.en_US/Catalog/ChemicalsNAFTA-/doc4/BASF/PRD/30085231/.pdf?asset_type=pi/pdf&language=EN&urn=urn:documen-tum:eCommerce_sol_EU:09007bb280022b53.pdf >] (Year: 2004).
Bondaryk et al. Postep. Derm. Alergol., 2013, vol. 5, pp. 293-301.
Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
csabiotech.com, Uncategorized: CSA Biotechnologies LLC. posted by admin on Apr. 5, 2011 (Year: 2011).
Czernomysy-Furowicz et al. Etiological agents of mastitis in dairy cows on a farm in the West Pomeranian Region. Acta Sci. Pol., Zootechnica 7(1) 2008, 3-10.
Dean et al.; Flavor Associated with Fish Meal in Diets Fed to Broiler Chickens; 1968; Can. J. Animal Sci.; 49:11-15 (Year: 1968).
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Jacob; Feeding Fishmeal to Poultry; https://articles.extension.org/pages/67357/feeding-fishmeal-to-poultry; May 5, 2015; accessed Sep. 10, 2018 (Year: 2015).
K. Leszczynska et al., "Potential of ceragin CSA-13 and its mixture with pluronic F-127 as treatment of topical bacterial infections", Journal of Applied Microbiology, vol. 110, No. 1, Oct. 21, 2010, pp. 229-238.
Kaltsas et al., Endocrine-Related Cancer (2005) 12 683-699.
Eszczynska et al. (J Antimicrob Chemother, published Nov. 7, 2012), Bacterial activity of cationic lipids, pp. 1-9).
No author listed. Novel antibiotic coating shows potential for use on surgical implants. Healio website. Dec. 21, 2005. healio.com/orthopedics/news/online/%7BdcOe6031-1f10-4b3c-abf6-f50b9cfd683f%7D/novel-antibiotic-coating-shows-potential-for-use-on-surgical-implants. Accessed Jun. 2, 2019. (Year: 2005).
Notice of Allowance received for U.S. Appl. No. 14/257,776, dated Mar. 25, 2016.
Office Action received for U.S. Appl. No. 14/257,776, dated Apr. 16, 2015.
Oxford Dictionaries (on-line) definition of Adsorb ([Retrieved from internet <URL: http://www.oxforddictionaries.com/us/definition/american_english/adsorb >] [Downloaded Mar. 10, 2015]).
Perry et al., "Assessing peri-implant tissue infection prevention in a percutaneous model", Journal of Biomedical Materials Research Part B: Applied Biomaterials, vol. 028, Nov. 19, 2009, pp. 397-408.
Pollard et al. (J Antimicrob Chemother 2012; 67:2665-2672).
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Sigma-Aldrich, Poly(ethylene-co-vinyl acetate), [Retrieved from internet <URL: http://www.sigmaaldrich.com/catalog/product/aldrich/340502?lang=- en®ion=US >], [Downloaded Jul. 22, 2016], excerpt in action.
Staphylococcal Infections (Electronic Resource; Merck Manual). Retrieved on Jul. 3, 2017: [http://www.merckmanuals.com/professional/infectious-diseases/gram-positive-cocci/staphylococcal-infections].
U.S. Appl. filed Apr. 22, 2016, Savage et al., U.S. Appl. No. 15/135,900.
U.S. Appl. filed Apr. 22, 2016, Savage et al., U.S. Appl. No. 15/135,928.
U.S. Appl. filed Apr. 22, 2016, Savage et al., U.S. Appl. No. 15/135,969.
U.S. Appl. filed Apr. 7, 2017, Savage., U.S. Appl. No. 15/481,184.
U.S. Appl. filed Apr. 7, 2017, Savage., U.S. Appl. No. 15/481,884.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 20, 2018, Savage., U.S. Appl. No. 15/926,534.
U.S. Appl. filed Mar. 21, 2016, Beus et al., U.S. Appl. No. 15/076,313.
U.S. Appl. filed Mar. 23, 2018, Savage, Paul B., U.S. Appl. No. 15/934,534.
U.S. Appl. filed Mar. 9, 2017, Savage et al., U.S. Appl. No. 15/454,135.
U.S. Appl. filed May 3, 2017, Savage et al., U.S. Appl. No. 15/585,632.
U.S. Appl. filed Sep. 20, 2016, Genberg et al., U.S. Appl. No. 15/270,876.
U.S. Appl. No. 13/841,549, filed Mar. 15, 2013, Office Action dated Apr. 23, 2015.
U.S. Application filed Feb. 17, 2015, by Savage, U.S. Appl. No. 14/624,200.
U.S. Application filed Mar. 10, 2015, by Darien et al., U.S. Appl. No. 14/642,905.
U.S. Application filed Oct. 25, 2016, by Vazquez et al., U.S. Appl. No. 15/333,514.
U.S. Appl. No. 13/288,902, filed Nov. 3, 2011, Notice of Allowance dated Aug. 9, 2013.
Zaragoza Dorwald, Side Reactions in Organic Synthesis, 2005, Wiley-VCH Verlag GmbH & Co. KGaA, Weinheim, Preface. p. IX.
BASF, [Retrieved from internet <URL:https://worldaccount.basf.com/wa/NAFTA.about.en_US/Catalog/ChemicalsNAFTA-/doc4/BASF/PRD/30085231/.pdf?asset_type=pi/pdf&language=EN&urn=um:documen-tum:eCommerce_sol_EU:09007bb280022b53.pdf >] (Year: 2004).
csabiotech.com, Uncategorized: CSA Biotecfinologies LLC. posted by admin on Apr. 5, 2011 (Year: 2011).
Czemomysy-Furowicz et al. Etiological agents of mastitis in dairy cows on a farm in the West Pomeranian Region. Acta Sci. Pol., Zootechnica 7(1) 2008, 3-10.
Sigma-Aldrich, Poly(ethylene-co-vinyl acetate), [Retrieved from internet <URL:http://www.sigmaaldrich.com/catalog/product/aldrich/340502?lang—en (Registered) ion=US >], [Downloaded Jul. 22, 2016], excerpt in action.
Graterol et al., "Ultrastructural changes in premalignant and malignant lesions of the uterine cervix with papillomavirus infection", Journal of Cancer Research and Experimental Oncology, vol. 2, No. 3, Sep. 2010, pp. 35-42.
Hao et al., "A Phase I and Pharmacokinetic Study of Squalamine, an Aminosterol Angiogenesis Inhibitor", Clin Cancer Res, vol. 9, 2003, pp. 2465-2471.
Kwon, Ed., Polymeric Drug Delivery Systems, Taylor & Francis Group, LLC; pp. 1-653, 2005, pp. 350-351.

(56) References Cited

OTHER PUBLICATIONS

Lai XZ ( Ceragenins: cholic acid-based mimics of antimicrobial peptides. Acc Chern Res. Oct.2008;41 (10): 1233-40. doi: 10.1021/ar700270t. Epub Jul. 11, 2008. PMID: 18516297.

McIntosh et al., "Towards Non-Invasive Screening of Skin Lesions by Near-Infrared Spectroscopy", The Journal of Investigative Dermatology, vol. 116, No. 1, 2001, pp. 175-181.

P B Savage et al: "Thin Films Containing Ceragenins Prevent Biofilm Formation on Endotracheal Tubes", 9th International Federation of Infection Control Congress, Oct. 14, 2008 (Oct. 14, 2008), pp. 1-1, XP55016800, Santiago, Chile Retrieved from the Internet: URL:http://www.n8medical.com/PDF/EndotrachealTubePoster-IFIC.PDF[retrieve-d on Jan. 18, 2012].

Robert Bucki (Resistance of the antibacterial agent ceragenin CSA-13 to inactivation by DNA or F-actin and its activity in cystic fibrosis sputum, Journal of Antimicrobial Chemotherapy, vol. 60, Issue 3, Sep. 2007, pp. 535-545).

Schiller et al., "Potentiation of Platinum Antitumor Effects in Human Lung Tumor Xenografts by the Angiogenesis Inhibitor Squalamine: Effects on Tumor Neovascularizalion", Clin Cancer Res., vol. 5, 1999, pp. 4287-4294.

Bondaryk, M. et al., "Antifungal agents commonly used in the superficial and mucosal candidiasis treatment: mode of action and resistance development", Postep. Derm., Alergol., vol. 30, No. 5, pp. 293-301.

European Search Report received for EP Patent Application No. 20810836.5, dated Jun. 30, 2022, 7 pages.

Martin, L., WebMD, 2012, pp. 1-25.

U.S. Appl. No. 14/873,013, filed Oct. 1, 2015, Final Office Action dated Jul. 13, 2017.

Berge et al., Pharmaceutical salts. Journal of Pharmaceutical Sciences, vol. 66(1), pp. 1-19 (Year: 1977).

International Preliminary Report on Patentability received for PCT Patent Application No. PCT/US20/034297, dated Dec. 2, 2021, 6 pages.

Sentamilselvi et al., International Journal of Trichology, vol. 1, Issue 2, pp. 100-108, Jul. 2009.

\* cited by examiner

METHODS FOR TREATING INFLAMMATION, AUTOIMMUNE DISORDERS AND PAIN

BACKGROUND

Field

Cationic steroidal antimicrobials ("CSAs") for treating certain diseases and symptoms such as gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, and/or pain.

Description of the Related Art

Inflammation is a biological response to harmful stimuli, such as pathogens, damaged cells, or irritants. As such, inflammation is a major component of the nonspecific defense system. The classical signs of acute inflammation are pain (dolor), heat (calor), redness (rubor), swelling (tumor), and loss of function. Although infection is caused by a microorganism, inflammation is one of the responses by the infected subject to the pathogen.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process Progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Periodontal disease, such as gingivitis and periodontitis, is one of the most common diseases and its severe form is estimated to afflict 10% of the population of the United States. Bacterial invasion plays an essential role in periodontal disease. Bacteria also trigger the host tissue to express an immunoinflammatory response, and this process can lead to resorption of the alveolar bone, connective tissue loss, the formation of periodontal pockets, and eventually loss of teeth. Other diseases are characterized by a host's inflammatory response. Such diseases include, but are not limited to gastritis, colitis, ileitis, Crohn's disease, chronic inflammatory intestinal disease, inflammatory bowel syndrome, chronic inflammatory bowel disease, celiac disease, ulcerative colitis, gastric ulcers, peptic ulcers, buccal ulcers, nasopharyngeal ulcers, esophageal ulcers, duodenal ulcers, and gastrointestinal ulcers. Therefore, a need exists to develop new methods for treating such diseases.

Many, but not all, disorders responsible for an inflammatory response implicate autoimmune disorders. An autoimmune disorder is a condition that occurs when the immune system mistakenly attacks and destroys healthy body tissue. In patients with an autoimmune disorder, the immune system can't tell the difference between healthy body tissue and antigens. The result is an immune response that destroys normal body tissues. What causes the immune system to no longer tell the difference between healthy body tissues and antigens is unknown. One theory is that some microorganisms (such as bacteria or viruses) or drugs may trigger some of these changes, especially in people who have genes that make them more likely to get autoimmune disorders. Regardless, new treatments are needed to help patients suffering from such diseases.

As previously mentioned, pain is often a sign of acute inflammation (but not all pain is caused by inflammation). Pain may be divided into two general categories—acute and chronic. Acute pain is typically characterized by rapid its onset, intensity, and short duration. Chronic pain, however, tends to be persistent, such as pain associated with inflammation, arthritis, etc. Chronic pain may also cause individuals to exhibit enhanced sensitivity to painful stimulus (hyperalgesia); painful sensation to normally non-painful stimulus (allodynia); burning sensation; and unusual nociceptive descriptors (stabbing, sharp, throbbing, etc.). In addition, chronic pain may also have additional physiological consequences such as trigger point producing pain (myofascial pain or radicular pain) or sympathetic dystrophy (warm/cold extremities, joint stiffness, or bone demineralization). Although various methods and substances for treating pain exist, such methods are often an inconvenience or the substances impair the patient's motor functions and/or can lead to addiction. Moreover, many of the treatments for acute pain may be addictive and are, therefore, not appropriate for long term use. Thus, new pain treatments and substances are needed.

SUMMARY

Some embodiments describe a method of treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain, comprising: identifying a patient in need of treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain; and administering a therapeutically effective amount of at least one cationic steroid antimicrobial (CSA), or a pharmaceutically acceptable sat thereof.

In some embodiments, the CSA is a compound of Formula (I) or a pharmaceutically acceptable salt thereof:

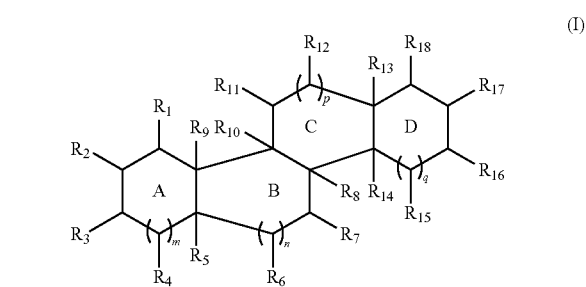

wherein rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N$—HC($Q_5$)-C(O)—, $H_2N$—HC($Q_5$)-C(O)—N(H)—, a substituted or unsubstituted azidoalkyloxy, a substituted or unsubstituted cyanoalkyloxy, P.G.-HN—HC($Q_5$)-C(O)—O—, a substituted or unsubstituted guanidinoalkyloxy, a substituted or unsubstituted quaternaryammoniumalkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N$—HC($Q_5$)-C(O)—O—, $H_2N$—HC($Q_5$)-C(O)—N(H)—, azidoalkyloxy, cyanoalkyloxy, P.G.-HN—HC($Q_5$)-C(O)—O—, guanidinoalkyloxy, and guanidinoalkylcarboxy, where Q5 is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxamido, a quaternaryammoniumalkylcarboxy, a substituted or unsubstituted di(alkyl)aminoalkyl, $H_2N$—HC($Q_5$)-C(O)—O—, $H_2N$—HC($Q_5$)-C(O)—N(H)—, azidoalkyloxy, cyanoalkyloxy, P.G.-HN—HC($Q_5$)-C(O)—O—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$)alkyl, a substituted or unsubstituted ($C_1$-$C_{18}$) hydroxyalkyl, a substituted or unsubstituted ($C_1$-$C_{18}$)alkyloxy-($C_1$-$C_{18}$)alkyl, a substituted or unsubstituted ($C_1$-$C_{18}$) alkylcarboxy-($C_1$-$C_{18}$)alkyl, a substituted or unsubstituted ($C_1$-$C_{18}$)alkylamino-($C_1$-$C_{18}$)alkyl, a substituted or unsubstituted ($C_1$-$C_{18}$)alkylamino-($C_1$-$C_{18}$)alkylamino, a substituted or unsubstituted ($C_1$-$C_{18}$)alkylamino-($C_1$-$C_{18}$)alkylamino-($C_1$-$C_{18}$)alkylamino, a substituted or unsubstituted ($C_1$-$C_{18}$)aminoalkyl, a substituted or unsubstituted aryl, a substituted or unsubstituted arylamino-($C_1$-$C_{18}$)alkyl, a substituted or unsubstituted ($C_1$-$C_{18}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{18}$)aminoalkyloxy, a substituted or unsubstituted ($C_1$-$C_{18}$)aminoalkyloxy-($C_1$-$C_{18}$)alkyl, a substituted or unsubstituted ($C_1$-$C_{18}$)aminoalkylcarboxy, a substituted or unsubstituted ($C_1$-$C_{18}$) aminoalkylaminocarbonyl, a substituted or unsubstituted ($C_1$-$C_{18}$)aminoalkylcarboxamido, a substituted or unsubstituted di($C_1$-$C_{18}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$)cyanoalkyloxy, P.G.-HN—HC($Q_5$)-C(O)—O—, a substituted or unsubstituted ($C_1$-$C_{18}$) guanidinoalkyloxy, a substituted or unsubstituted ($C_1$-$C_{18}$) quaternaryammoniumalkylcarboxy, and a substituted or unsubstituted ($C_1$-$C_{18}$) guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$)alkyl, a substituted or unsubstituted ($C_1$-$C_{18}$) hydroxyalkyl, a substituted or unsubstituted ($C_1$-$C_{18}$)alkyloxy-($C_1$-$C_{18}$)alkyl, a substituted or unsubstituted ($C_1$-$C_{18}$)aminoalkyl, a substituted or unsubstituted aryl, a substituted or unsubstituted ($C_1$-$C_{18}$)haloalkyl, a substituted or unsubstituted ($C_2$-$C_6$)alkenyl, a substituted or unsubstituted ($C_2$-$C_6$)alkynyl, oxo, a linking group attached to a second steroid, a substituted or unsubstituted ($C_1$-$C_{18}$)aminoalkyloxy, a substituted or unsubstituted ($C_1$-$C_{18}$)aminoalkylcarboxy, a substituted or unsubstituted ($C_1$-$C_{18}$)aminoalkylaminocarbonyl, a substituted or unsubstituted di($C_1$-$C_{18}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$)cyanoalkyloxy, P.G.-HN—HC($Q_5$)-C(O)—O—, a substituted or unsubstituted ($C_1$-$C_{18}$) guanidinoalkyloxy, and ($C_1$-$C_{18}$) guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$)aminoalkyl, a substituted or unsubstituted ($C_1$-$C_{18}$)aminoalkyloxy, a substituted or unsubstituted ($C_1$-$C_{18}$)alkylcarboxy-($C_1$-$C_{18}$)alkyl, a substituted or unsubstituted ($C_1$-$C_{18}$)alkylamino-($C_1$-$C_{18}$)alkylamino, a substituted or unsubstituted ($C_1$-$C_{18}$)alkylamino-($C_1$-$C_{18}$)alkylamino($C_1$-$C_{18}$)alkylamino, a substituted or unsubstituted ($C_1$-$C_{18}$)aminoalkylcarboxy, a substituted or unsubstituted arylamino($C_1$-$C_{18}$) alkyl, a substituted or unsubstituted ($C_1$-$C_{18}$)aminoalkyloxy($C_1$-$C_{18}$)aminoalkylaminocarbonyl, a substituted or unsubstituted ($C_1$-$C_{18}$)aminoalkylaminocarbonyl, a substituted or unsubstituted ($C_1$-$C_{18}$)aminoalkylcarboxyamido, a a substituted or unsubstituted ($C_1$-$C_{18}$) quaternaryammoniumalkylcarboxy, a substituted or unsubstituted di($C_1$-$C_{18}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$)cyanoalkyloxy, P.G.-HN—HC($Q_5$)-C(O)—O—, a substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, ($C_1$-$C_{18}$)alkylamino-($C_1$-$C_{18}$)alkylamino-($C_1$-$C_{18}$)alkylamino, an unsubstituted ($C_1$-$C_{18}$) aminoalkyl, an unsubstituted aryl, an unsubstituted arylamino-($C_1$-$C_{18}$)alkyl, oxo, an unsubstituted ($C_1$-$C_{18}$) aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$)alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$) aminoalkyl, an unsubstituted aryl, an unsubstituted arylamino-($C_1$-$C_{18}$)alkyl, oxo, an unsubstituted ($C_1$-$C_{18}$)aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$)aminoalkyl, an unsubstituted aryl, an unsubstituted arylamino-($C_1$-$C_{18}$)alkyl, oxo, an unsubstituted ($C_1$-$C_{18}$) aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy.

In some embodiments, the CSA, or a pharmaceutically acceptable salt thereof, is selected from the compound of Formula (II):

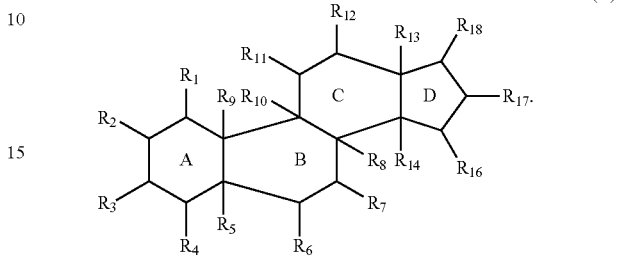

(II)

In some embodiments, rings A, B, C, and D are independently saturated.

In some embodiments, $R_3$, $R_7$, $R_{12}$, and $R_{18}$ are independently selected from the group consisting of hydrogen, an unsubstituted ($C_1$-$C_{18}$)alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$)aminoalkyl, an unsubstituted arylamino-($C_1$-$C_{18}$)alkyl, an unsubstituted ($C_1$-$C_{18}$)aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)amino alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$)alkyl.

In some embodiments, $R_3$, $R_7$, $R_{12}$, and $R_{18}$ are independently selected from the group consisting of hydrogen, an unsubstituted ($C_1$-$C_6$)alkyl, unsubstituted ($C_1$-$C_6$) hydroxyalkyl, unsubstituted ($C_1$-$C_{16}$)alkyloxy-($C_1$-$C_5$)alkyl, unsubstituted ($C_1$-$C_{16}$)alkylcarboxy-($C_1$-$C_5$)alkyl, unsubstituted ($C_1$-$C_{16}$)alkylamino-($C_1$-$C_5$)alkyl, ($C_1$-$C_{16}$)alkylamino-($C_1$-$C_5$)alkylamino, unsubstituted ($C_1$-$C_{16}$)alkylamino-($C_1$-$C_{16}$)alkylamino-($C_1$-$C_5$)alkylamino, an unsubstituted ($C_1$-$C_{16}$)aminoalkyl, an unsubstituted arylamino-($C_1$-$C_5$)alkyl, an unsubstituted ($C_1$-$C_5$)aminoalkyloxy, an unsubstituted ($C_1$-$C_{16}$)aminoalkyloxy-($C_1$-$C_5$)alkyl, an unsubstituted ($C_1$-$C_5$) aminoalkylcarboxy, an unsubstituted ($C_1$-$C_5$)aminoalkylaminocarbonyl, an unsubstituted ($C_1$-$C_5$) aminoalkylcarboxamido, an unsubstituted di($C_1$-$C_5$ alkyl)amino-($C_1$-$C_5$)alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl. In some embodiments, $R_3$, $R_7$, $R_{12}$, and $R_{18}$ are independently selected from the group consisting of aminoalkyloxy; aminoalkylcarboxy; alkylamino alkyl; alkoxycarbonylalkyl; alkylcarbonylalkyl; di(alkyl)aminoalkyl;

alkoxycarbonylalkyl; and alkylcarboxyalkyl. In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl. In some embodiments, $R_3$, $R_7$, and $R_{12}$ are the same. In some embodiments, $R_3$, $R_7$, and $R_{12}$ are aminoalkyloxy. In some embodiments, $R_{18}$ is alkylaminoalkyl. In some embodiments, $R_{18}$ is alkoxycarbonylalkyl. In some embodiments, $R_{18}$ is di(alkyl)aminoalkyl. In some embodiments, $R_{18}$ is alkylcarboxyalkyl. In some embodiments, $R_3$, $R_7$, and $R_{12}$ are aminoalkylcarboxy. In some embodiments, $R_{18}$ is alkylaminoalkyl. In some embodiments, $R_{18}$ is alkoxycarbonylalkyl. In some embodiments, $R_{18}$ is di(alkyl)aminoalkyl. In some embodiments, $R_{18}$ is alkylcarboxyalkyl. In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl. In some embodiments, m, n, and p, are each 1 and q is 0.

In some embodiments, the CSA, or a pharmaceutically acceptable salt thereof, is selected from the compound of Formula (III):

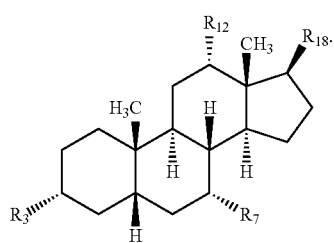

In some embodiments, the CSA, or a pharmaceutically acceptable salt thereof, is selected from the group consisting of:

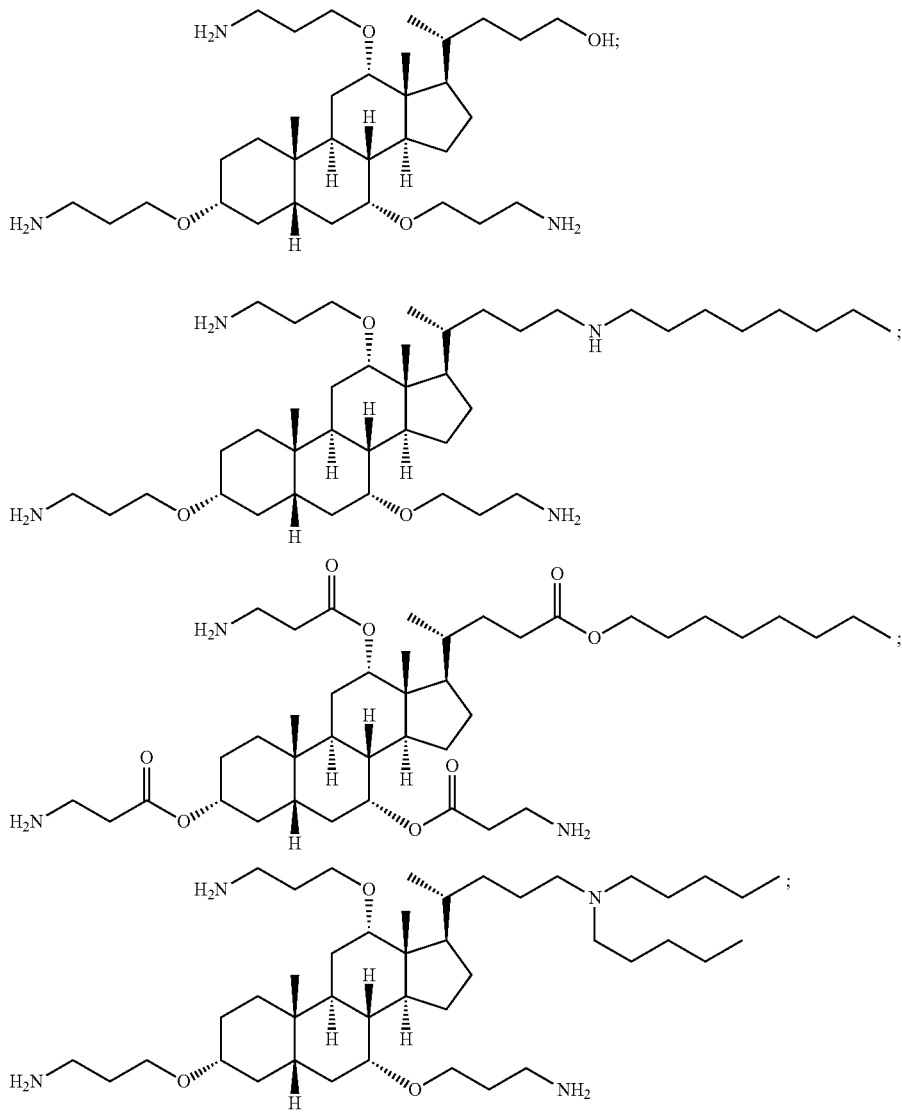

-continued
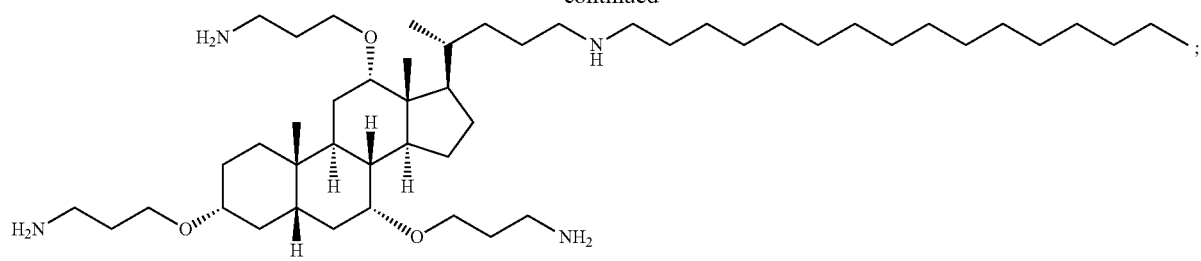
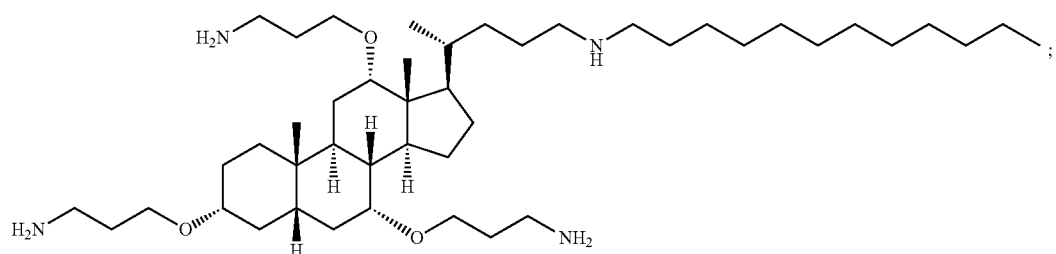
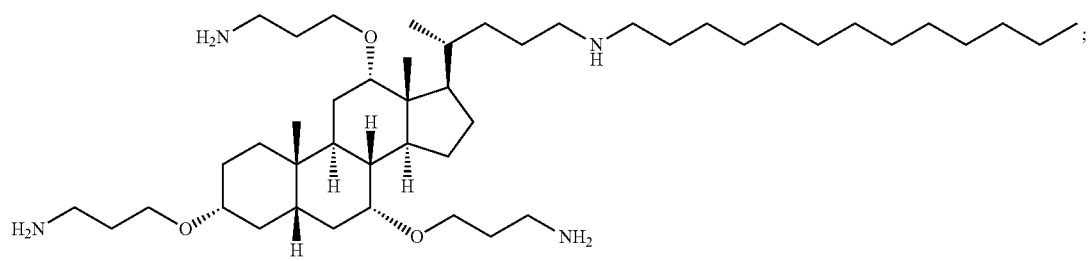
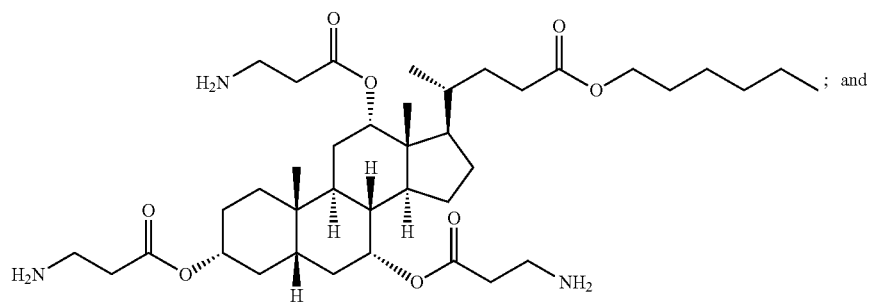; and
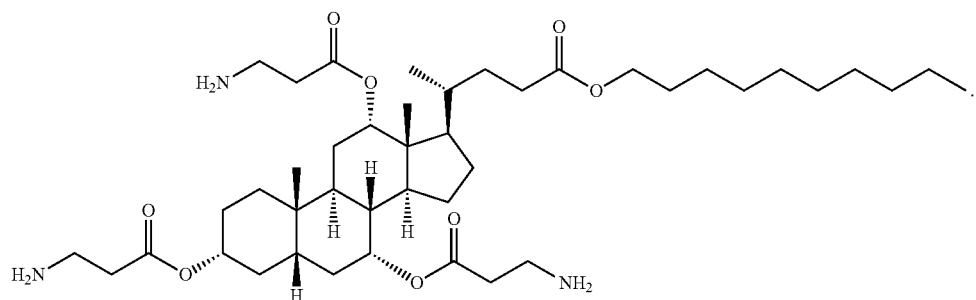.

In some embodiments, the compound of Formula (III), or a pharmaceutically acceptable salt thereof, is

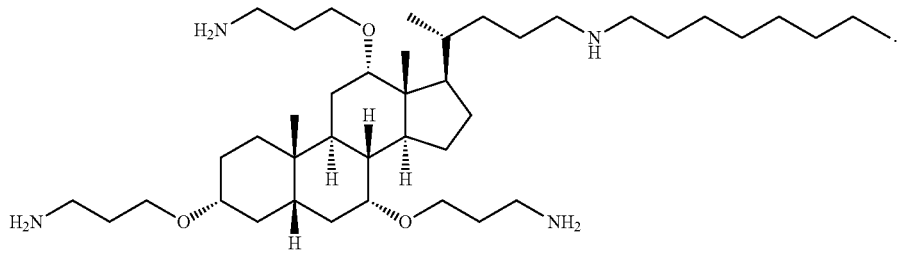

In some embodiments, the compound of Formula (III), or a pharmaceutically acceptable salt thereof, is

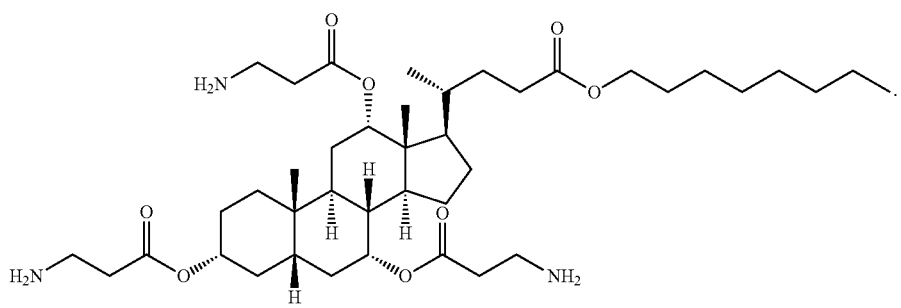

In some embodiments, the compound of Formula (III), or a pharmaceutically acceptable salt thereof, is

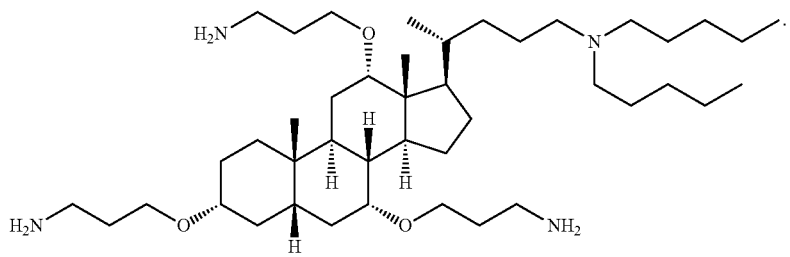

In some embodiments, the compound of Formula (III), or a pharmaceutically acceptable salt thereof, is

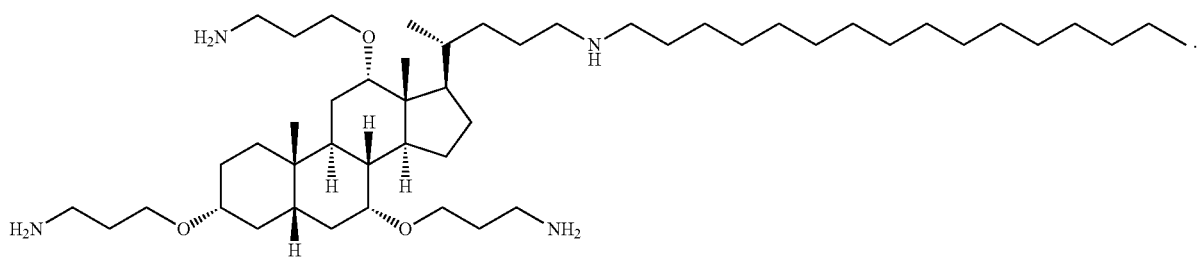

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. In some embodiments, the method further comprises administering an antibiotic to the patient. In some embodiments, the antibiotic is a non-CSA antibiotic.

In some embodiments, an antibiotic is further administered. In some embodiments, the antibiotic is selected from the group consisting of an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, and a tetracycline.

In some embodiments, the method further comprises administering a non-CSA anti-inflammatory agent.

In some embodiments, the CSA inhibits resorption of the alveolar bone. In some embodiments, the CSA inhibits inflammation. In some embodiments, the CSA inhibits inflammation mediated by a tumor necrosis factor.

In some embodiments, the CSA is complexed with albumin or a surfactant. In some embodiments, the CSA is complexed with one or more poloxamer surfactant. In some embodiments, the one or more poloxamer surfactant is a flake poloxamer. In some embodiments, the one or more poloxamer surfactant has a molecular weight of about 3600 g/mol for the central hydrophobic chain of polyoxypropylene and has about 70% polyoxyethylene content. In some embodiments, the ratio of the one or more poloxamer to CSA is between about 50:1 to about 1:50. In some embodiments, the ratio of the one or more poloxamer to CSA is between about 30:1 to about 3:1. In some embodiments, the one or more poloxamer is between about 10% to about 40% by weight of a formulation administered to the patient. In some embodiments, the one or more poloxamer is between about 20% to about 30% by weight of the formulation. In some embodiments, the CSA is administered in a formulation containing less than about 20% by weight of CSA.

In some embodiments, the CSA is selected by measuring a biomarker or subjecting a sample from the patient to a companion diagnostic device in the patient. In some embodiments, the biomarker is a cellular response to the CSA or the companion diagnostic device measures a cellular response to the CSA. In some embodiments, the cellular response is a change in mRNA levels associated with inflammation.

In some embodiments, the disease is gingivitis. In some embodiments, the disease is periodontitis. In some embodiments, the disease is gastritis. In some embodiments, the disease is colitis. In some embodiments, the disease is ileitis. In some embodiments, the disease is Crohn's disease. In some embodiments, the disease is chronic inflammatory intestinal disease. In some embodiments, the disease is inflammatory bowel syndrome. In some embodiments, the disease is chronic inflammatory bowel disease. In some embodiments, the disease is celiac disease. In some embodiments, the disease is ulcerative colitis. In some embodiments, the disease is a gastric ulcer. In some embodiments, the disease is a peptic ulcer. In some embodiments, the disease is a buccal ulcer. In some embodiments, the disease is a nasopharyngeal ulcer. In some embodiments, the disease is an esophageal ulcer. In some embodiments, the disease is a duodenal ulcer. In some embodiments, the disease is a gastrointestinal ulcer. In some embodiments, the diseases is an autoimmune disorder. In some embodiments, the symptom is pain. In some embodiments, the symptom is pain caused, related, or associated with a disease selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer.

In some embodiments, the pain is nociceptive, neuropathic, phantom, psychogenic, breakthrough pain, or incident pain. In some embodiments, the pain is acute or chronic. In some embodiments, the treating, reducing, or preventing a disease or symptom is independent of CSA antibiotic activity. In some embodiments, the patient is a mammal. In some embodiments, the mammal is a human. Some embodiments describe a CSA composition, comprising CSA and one or more poloxymers. In some embodiments, the composition contains less than about 20% by weight of CSA; and between about 10% to about 40% by weight of one or more poloxymer. In some embodiments, the composition contains less than about 10% by weight of CSA; and between about 20% to about 30% by weight of one or more poloxymer. In some embodiments, the ratio of the one or more poloxamer to CSA is between about 30:1 to about 3:1. In some embodiments, the one or more poloxamer surfactant is a flake poloxamer. In some embodiments, the one or more poloxamer surfactant has a molecular weight of about 3600 g/mol for the central hydrophobic chain of polyoxypropylene and has about 70% polyoxyethylene content. In some embodiments, the composition further comprises albumin.

DETAILED DESCRIPTION

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

DEFINITIONS

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$, $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO\text{—}$, $R_b(CH_2)_nO\text{—}$, $R_cC(O)O(CH_2)_pO\text{—}$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3\text{—}$, $CH_3CH_2\text{—}$, $CH_3CH_2CH_2\text{—}$, $(CH_3)_2CH\text{—}$, $CH_3CH_2CH_2CH_2\text{—}$, $CH_3CH_2CH(CH_3)\text{—}$ and $(CH_3)_3C\text{—}$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as $\text{—}CH_2\text{—}$ tethering groups, forming bonds to connect molecular fragments via their terminal carbon atoms. Examples include but are not limited to methylene ($\text{—}CH_2\text{—}$), ethylene ($\text{—}CH_2CH_2\text{—}$), propylene ($\text{—}CH_2CH_2CH_2\text{—}$), and butylene ($\text{—}CH_2CH_2CH_2CH_2\text{—}$). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy(isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

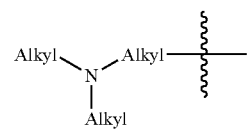

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

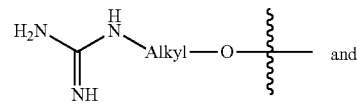

-continued

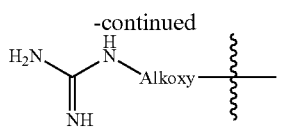

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

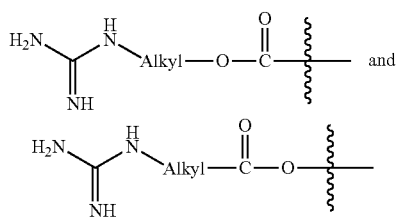

with the term alkyl as defined herein.

As used herein, "quaternaryammoniumalkylcarboxy" refers to a quaternized amino group connected, as a substituent, to an alkyl group connected, as a substituent, to a carboxy group. Examples include

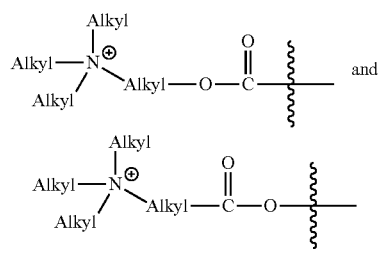

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is $(C_1\text{-}C_{10})$alkyloxy-$(C_1\text{-}C_{10})$alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Compounds:

Compounds useful in accordance with this disclosure are described herein, both generically and with particularity, and in U.S. Pat. Nos. 6,350,738, 6,486,148, 6,767,904, 7,598,234, and 7,754,705, which are incorporated herein by reference. Compounds include steroid derivatives, such as cationic steroid antimicrobials ("CSAs" and also referred to as ceragenins or cationic selective antimicrobials) that exhibit one or more anti-inflammatory properties, autoimmune relieving properties, or pain relieving properties relevant to treating, reducing, or preventing a disease or symptom such as gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, and/or pain. The skilled artisan will recognize the compounds within the generic formula set forth herein. Additional compounds of the disclosure having one or more anti-inflammatory properties, autoimmune relieving properties, or pain relieving properties relevant to treating, reducing, or preventing a disease or symptom such as gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, and/or pain are described and can be characterized using the assays set forth herein and in the art.

Methods and Uses:

We have discovered that CSAs are useful for modulating inflammatory responses. Accordingly, disclosed herein are methods of treating, reducing, or inhibiting inflammation or inflammatory responses by administering one or more CSAs to a patient in need thereof. During the course of our discovery, we also found that CSAs are useful for treating pain associated with inflammation. In particular, we have discovered that CSAs are useful for treating one or more of gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer or a gastrointestinal ulcer, or pain associated with said diseases. Several of these diseases are autoimmune disorders. As previously and generally described, an autoimmune disorder involves a condition that occurs when the immune system mistakenly attacks and destroys healthy body tissue. Such autoimmune disorders include celiac disease, certain types of arthritis (such as reactive and rheumatoid), Graves diseases, etc.

Disclosed herein are methods of treating diseases selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, or a gastrointestinal ulcer comprising identifying a patient in need of treatment and administering a therapeutically effective amount of at least one cationic steroid antimicrobial (CSA), or a pharmaceutically acceptable salt thereof. Disclosed herein are also methods of reducing, treating, or alleviating pain associated, derived, or caused by gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer or a gastrointestinal ulcer. Disclosed herein are also methods of reducing, treating, or alleviating an autoimmune disorder.

Moreover, our initial observations regarding pain have led to the surprising discovery that CSAs are effective at managing pain in general, as opposed to pain associated with inflammation. Accordingly, disclosed herein are methods of treating, reducing, or preventing pain comprising identifying a patient in need of said treatment and administering a therapeutically effective amount of at least one cationic steroid antimicrobial (CSA), or a pharmaceutically acceptable sat thereof. In some embodiments, the pain is nociceptive, neuropathic, phantom, psychogenic, breakthrough pain, or incident pain. In some embodiments, the pain is acute. In other embodiments, the pain is chronic. In other embodiments, the pain is a trigger point producing pain. In other embodiments, the pain is a sympathetic dystrophy. In some embodiments, the patient suffering from pain has tried one or more unsuccessful pain remedies (such as acupuncture or drugs such as opioids).

Some embodiments are a method of treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain, comprising: identifying a patient in need of treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain; and administering a therapeutically effective amount of at least one cationic steroid antimicrobial (CSA), or a pharmaceutically acceptable sat thereof.

In some embodiments, a therapeutically effective amount of at least one cationic steroid antimicrobial (CSA), or a pharmaceutically acceptable salt thereof is administered to treat oral inflammatory diseases. Such diseases specifically include gingivitis and periodontitis. In some embodiments, CSAs are administered to prevent such oral inflammatory diseases, specifically gingivitis or periodontitis. In other embodiments, a therapeutically effective amount of at least one cationic steroid antimicrobial (CSA), or a pharmaceutically acceptable salt thereof is administered to treat gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, an autoimmune disorder, and a gastrointestinal ulcer. In some embodiments, CSAs are administered to prevent such diseases, specifically gastritis, colitis, ileitis, and ulcer development. In some embodiments, CSAs are administered to treat pain associated with these diseases.

Some embodiments disclosed herein relate to a method of treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, or pain comprising administering a compound of Formula (I) or a pharmaceutically acceptable salt thereof:

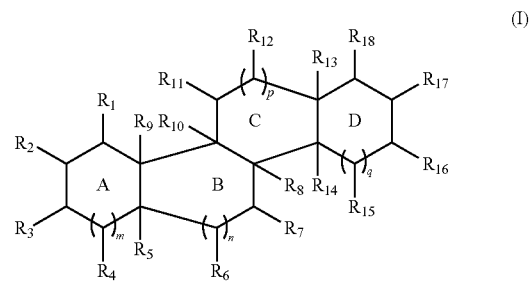

wherein rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, substituted or unsubstituted quaternaryammoniumalkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, and substituted or unsubstituted guanidinoalkylcarboxy, where Q5 is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxamido, a substituted or unsubstituted quaternaryammoniumalkylcarboxy, a substituted or unsubstituted di(alkyl)aminoalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$)alkyl, substituted or unsubstituted ($C_1$-$C_{18}$) hydroxyalkyl, substituted or unsubstituted ($C_1$-$C_{18}$)alkyloxy-($C_1$-$C_{18}$)alkyl, substituted or unsubstituted ($C_1$-$C_{18}$) alkylcarboxy-($C_1$-$C_{18}$)alkyl, substituted or unsubstituted ($C_1$-$C_{18}$)alkylamino-($C_1$-$C_{18}$)alkyl, substituted or unsubstituted ($C_1$-$C_{18}$)alkylamino-($C_1$-$C_{18}$)alkylamino, substituted or unsubstituted ($C_1$-$C_{18}$)alkylamino-($C_1$-$C_{18}$)alkylamino-($C_1$-$C_{18}$)alkylamino, a substituted or unsubstituted ($C_1$-$C_{18}$) aminoalkyl, a substituted or unsubstituted aryl, a substituted or unsubstituted arylamino-($C_1$-$C_{18}$)alkyl, substituted or unsubstituted ($C_1$-$C_{18}$)haloalkyl, substituted or unsubstituted ($C_2$-$C_6$)alkenyl, substituted or unsubstituted ($C_2$-$C_6$) alkynyl, oxo, a linking group attached to a second steroid, a substituted or unsubstituted ($C_1$-$C_{18}$)aminoalkyloxy, a substituted or unsubstituted ($C_1$-$C_{18}$)aminoalkyloxy-($C_1$-$C_{18}$) alkyl, a substituted or unsubstituted ($C_1$-$C_{18}$)aminoalkylcarboxy, a substituted or unsubstituted ($C_1$-$C_{18}$) aminoalkylaminocarbonyl, a substituted or unsubstituted ($C_1$-$C_{18}$)aminoalkylcarboxamido, a substituted or unsubstituted di($C_1$-$C_{18}$ alkyl)aminoalkyl, $H_2N$—$HC(Q_5)$-$C(O)$—O—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$)cyanoalkyloxy, P.G.-HN—$HC(Q_5)$-$C(O)$—O—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$)alkyl, substituted or unsubstituted ($C_1$-$C_{18}$) hydroxyalkyl, substituted or unsubstituted ($C_1$-$C_{18}$)alkyloxy-($C_1$-$C_{18}$)alkyl, a substituted or unsubstituted ($C_1$-$C_{18}$)aminoalkyl, a substituted or unsubstituted aryl, substituted or unsubstituted ($C_1$-$C_{18}$)haloalkyl, substituted or unsubstituted ($C_2$-$C_6$)alkenyl, substituted or unsubstituted ($C_2$-$C_6$)alkynyl, oxo, a linking group attached to a second steroid, a substituted or unsubstituted ($C_1$-$C_{18}$)aminoalkyloxy, a substituted or unsubstituted ($C_1$-$C_{18}$)aminoalkylcarboxy, a substituted or unsubstituted ($C_1$-$C_{18}$)aminoalkylaminocarbonyl, di($C_1$-$C_{18}$ alkyl)aminoalkyl, $H_2N$—$HC(Q_5)$-$C(O)$—O—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$)cyanoalkyloxy, P.G.-HN—$HC(Q_5)$-$C(O)$—O—, substituted or unsubstituted ($C_1$-$C_{18}$) guanidinoalkyloxy, and substituted or unsubstituted ($C_1$-$C_{18}$) guanidinoalkylcarboxy, where $Q_5$ is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$)aminoalkyl, a substituted or unsubstituted ($C_1$-$C_{18}$)aminoalkyloxy, substituted or unsubstituted ($C_1$-$C_{18}$)alkylcarboxy-($C_1$-$C_{18}$)alkyl, substituted or unsubstituted ($C_1$-$C_{18}$)alkylamino-($C_1$-$C_{18}$)alkylamino, substituted or unsubstituted ($C_1$-$C_{18}$)alkylamino-($C_1$-$C_{18}$)alkylamino($C_1$-$C_{18}$)alkylamino, a substituted or unsubstituted ($C_1$-$C_{18}$)aminoalkylcarboxy, a substituted or unsubstituted arylamino($C_1$-$C_{18}$)alkyl, a substituted or unsubstituted ($C_1$-$C_{18}$)aminoalkyloxy($C_1$-$C_{18}$)aminoalkylaminocarbonyl, a substituted or unsubstituted ($C_1$-$C_{18}$)aminoalkylaminocarbonyl, a substituted or unsubstituted ($C_1$-$C_{18}$)aminoalkylcarboxyamido, a substituted or unsubstituted ($C_1$-$C_{18}$) quaternaryammoniumalkylcarboxy, substituted or unsubstituted di($C_1$-$C_{18}$ alkyl)aminoalkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$)cyanoalkyloxy, P.G.-HN—HC(Q5)-C(O)—O—, substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$)aminoalkyl, an unsubstituted aryl, an unsubstituted arylamino-($C_1$-$C_{18}$)alkyl, oxo, an unsubstituted ($C_1$-$C_{18}$) aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$)alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$)aminoalkyl, an unsubstituted aryl, an unsubstituted arylamino-($C_1$-$C_{18}$)alkyl, oxo, an unsubstituted ($C_1$-$C_{18}$)aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$)alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino, an unsubstituted ($C_1$-$C_{18}$)aminoalkyl, an unsubstituted aryl, an unsubstituted arylamino-($C_1$-$C_{18}$)alkyl, oxo, an unsubstituted ($C_1$-$C_{18}$) aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy.

In some embodiments, the CSA, or pharmaceutically acceptable salts thereof of Formula (I), is represented by Formula (II):

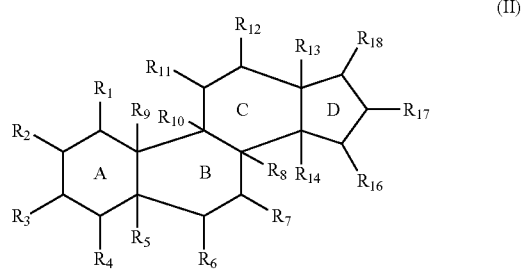

(II)

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, $R_3$, $R_7$, $R_{12}$, and $R_{18}$ are independently selected from the group consisting of hydrogen, an unsubstituted ($C_1$-$C_{18}$)alkyl, unsubstituted ($C_1$-$C_{18}$) hydroxyalkyl, unsubstituted ($C_1$-$C_{18}$)alkyloxy-($C_1$-$C_{18}$)alkyl, unsubstituted ($C_1$-$C_{18}$)alkylcarboxy-($C_1$-$C_{18}$)alkyl, unsubstituted ($C_1$-$C_{18}$)alkylamino-($C_1$-$C_{18}$)alkyl, unsubstituted ($C_1$-$C_{18}$)alkylamino-($C_1$-$C_{18}$)alkylamino, unsubstituted ($C_1$-$C_{18}$)alkylamino-($C_1$-$C_{18}$)alkylamino-($C_1$-$C_{18}$)alkylamino, an unsubstituted ($C_1$-$C_{18}$)aminoalkyl, an unsubstituted arylamino-($C_1$-$C_{18}$)alkyl, an unsubstituted ($C_1$-$C_{18}$)aminoalkyloxy, an unsubstituted ($C_1$-$C_{18}$)aminoalkyloxy-($C_1$-$C_{18}$)alkyl, an unsubstituted ($C_1$-$C_{18}$)aminoalkylcarboxy, an unsubstituted ($C_1$-$C_{18}$)aminoalkylaminocarbonyl, an unsubstituted ($C_1$-$C_{18}$)aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$)alkyl.

In some embodiments, $R_3$, $R_7$, $R_{12}$, and $R_{18}$ are independently selected from the group consisting of hydrogen, an unsubstituted ($C_1$-$C_6$)alkyl, unsubstituted ($C_1$-$C_6$) hydroxyalkyl, unsubstituted ($C_1$-$C_{16}$)alkyloxy-($C_1$-$C_5$)alkyl, unsubstituted ($C_1$-$C_{16}$)alkylcarboxy-($C_1$-$C_5$)alkyl, unsubstituted ($C_1$-$C_{16}$)alkylamino-($C_1$-$C_5$)alkyl, unsubstituted ($C_1$-$C_{16}$)alkylamino-($C_1$-$C_5$)alkylamino, unsubstituted ($C_1$-$C_{16}$)alkylamino-($C_1$-$C_{16}$)alkylamino-($C_1$-$C_5$)alkylamino, an unsubstituted ($C_1$-$C_{16}$)aminoalkyl, an unsubstituted arylamino-($C_1$-$C_5$)alkyl, an unsubstituted ($C_1$-$C_5$)aminoalkyloxy, an unsubstituted ($C_1$-$C_{16}$)aminoalkyloxy-($C_1$-$C_5$)alkyl, an unsubstituted ($C_1$-$C_5$)aminoalkylcarboxy, an unsubstituted ($C_1$-$C_5$)aminoalkylaminocarbonyl, an unsubstituted ($C_1$-$C_5$) aminoalkylcarboxamido, an unsubstituted di($C_1$-$C_5$ alkyl)amino-($C_1$-$C_5$)alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_3$, $R_7$, and $R_{12}$ are aminoalkylcarboxy.

In some embodiments, $R_{18}$ is alkylaminoalkyl.

In some embodiments, $R_{18}$ is alkoxycarbonylalkyl.

In some embodiments, $R_{18}$ is di(alkyl)aminoalkyl.

In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, m, n, and p are each 1 and q is 0.

In some embodiments, the CSA, or pharmaceutically acceptable salts thereof of Formula (I) is represented by Formula (III):

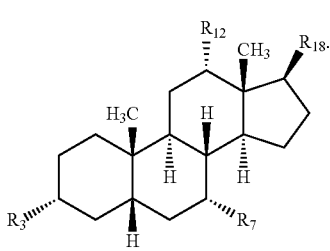

In some embodiments, the CSA, or a pharmaceutically acceptable salt thereof, is:

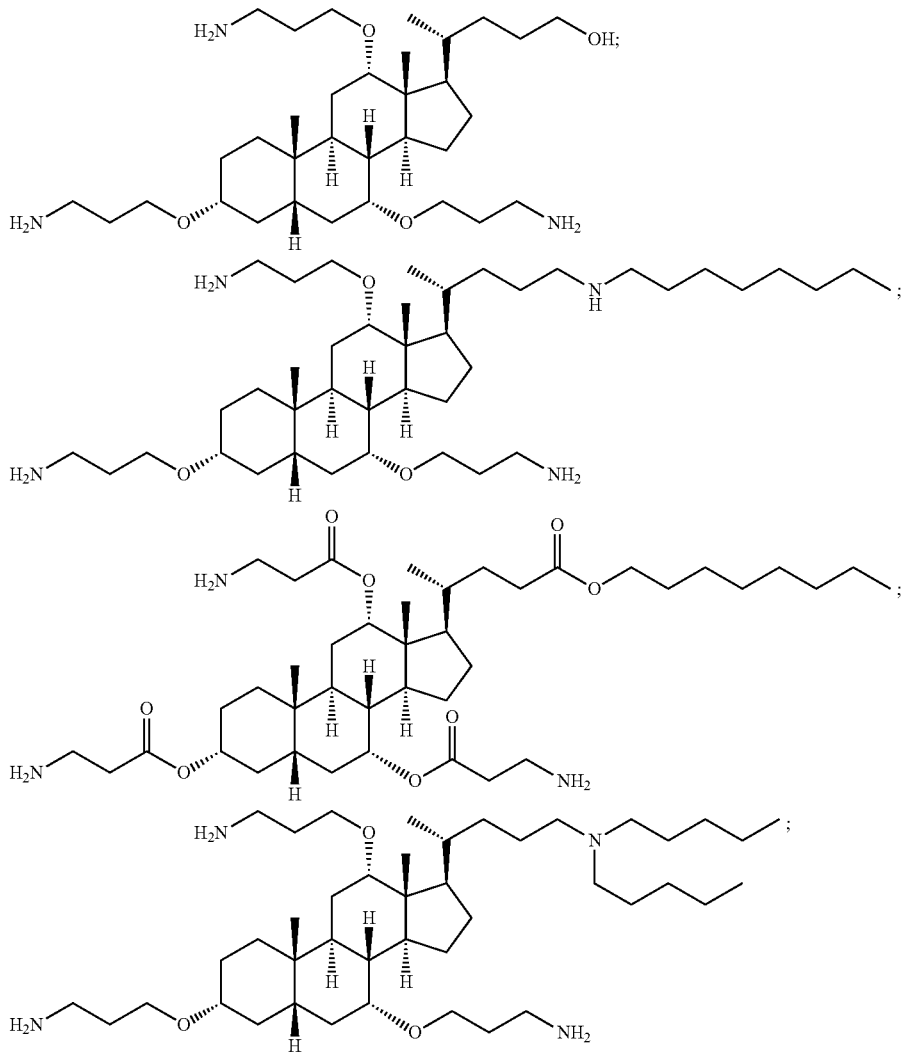

-continued
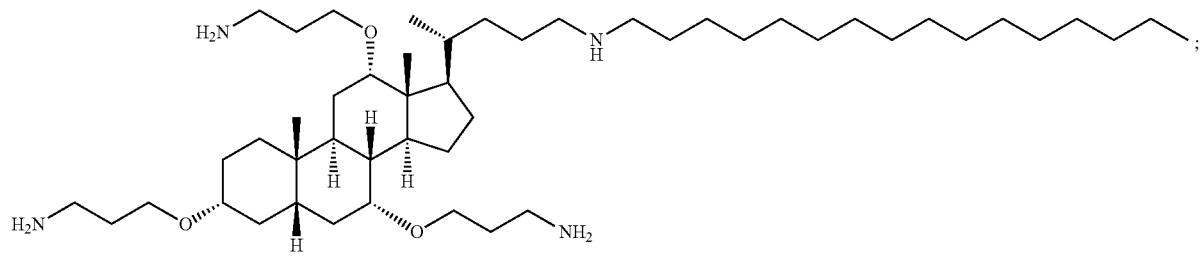
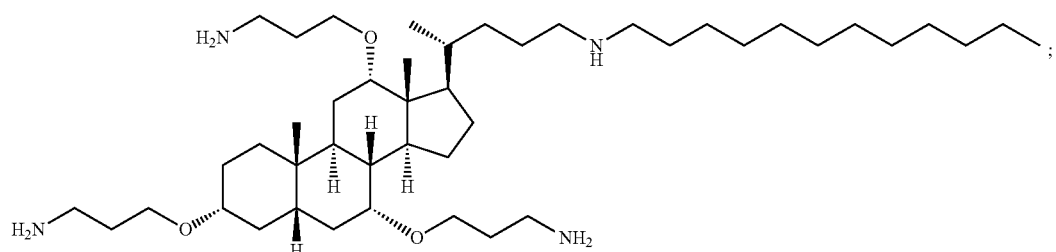
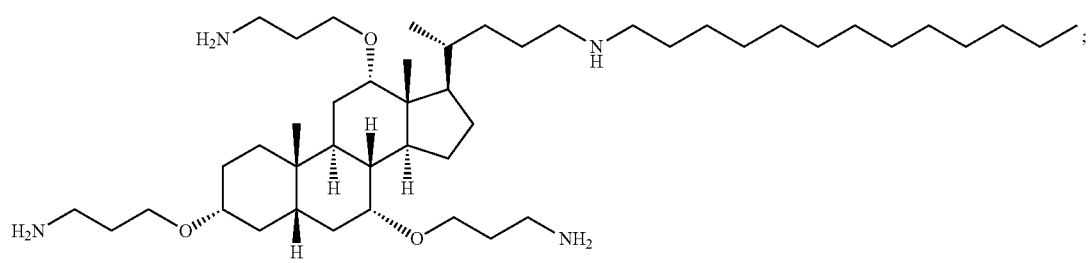
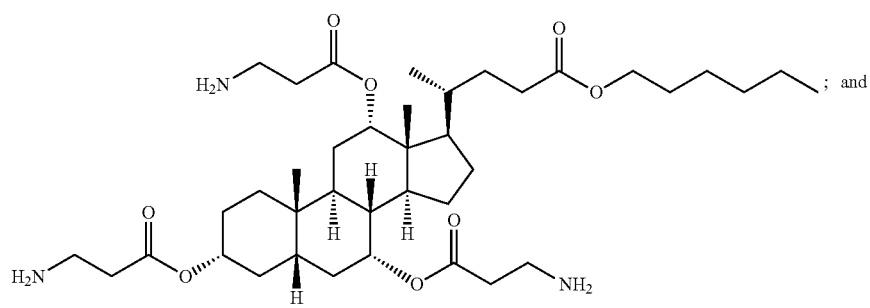
; and
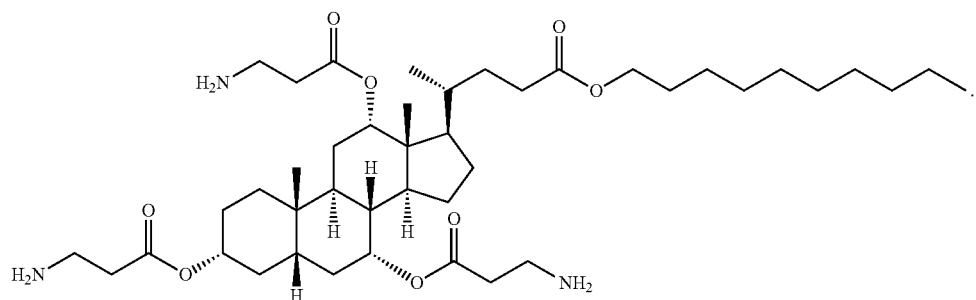

In some embodiments, the CSA, or a pharmaceutically acceptable salt thereof, is

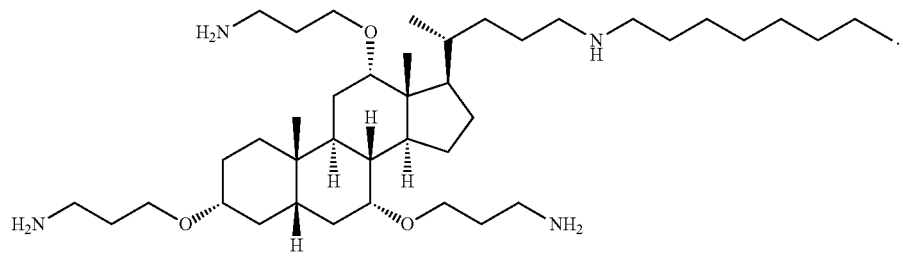

In other embodiments, the CSA, or a pharmaceutically acceptable salt thereof, is

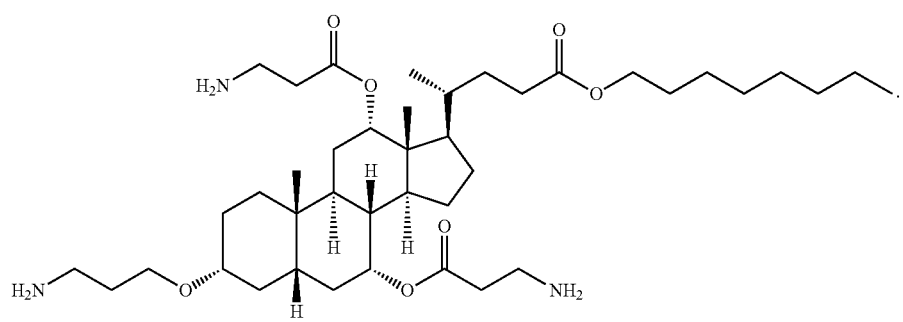

In other embodiments, the CSA, or a pharmaceutically acceptable salt thereof, is

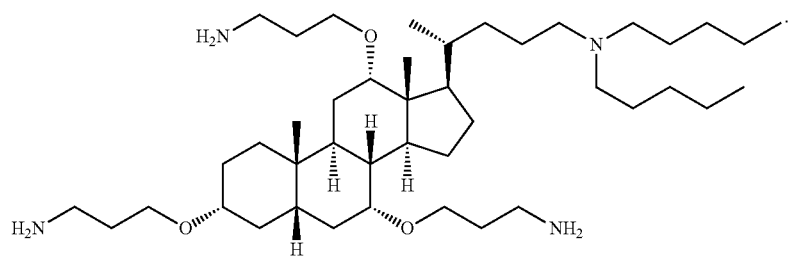

In other embodiments, the CSA, or a pharmaceutically acceptable salt thereof, is

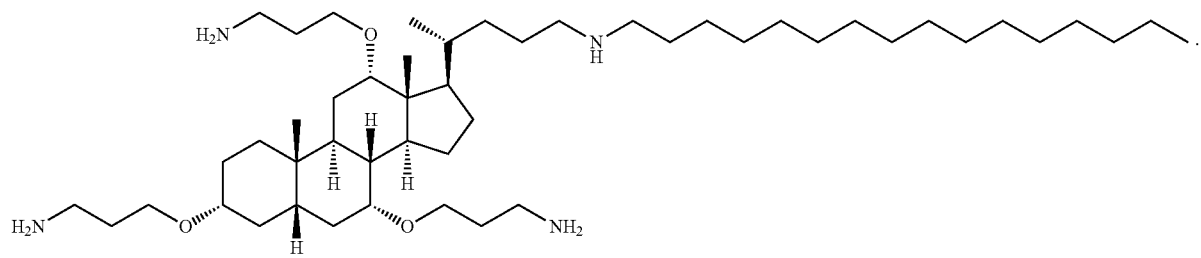

In some embodiments, the CSA prevents, inhibits, or reduces the symptoms associated with a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, an autoimmune disorder, pain, or pain associated with one or more of said diseases. For example, in some embodiments, the CSA inhibits inflammation associated with the aforementioned diseases.

In some embodiments, the CSA inhibits inflammation mediated by a tumor necrosis factor. In some embodiments, the CSA inhibits, reduces, or prevents inflammation of the periodontal ligament or the alveolar bone. In other embodiments, the CSA inhibits, reduces, or prevents resorption of alveolar bone. In some embodiments, the CSA inhibits, reduces, or prevents the episodic resorption of alveolar bone. In other embodiments, the CSA inhibits, reduces, or prevents the continuous resorption of alveolar bone. In some embodiments, the CSA promotes the regeneration of alveolar bone, periodontal ligament, or root cementum. In some embodiments, the CSA inhibits, reduces, or prevents pain caused by gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, an autoimmune disorder, and a gastrointestinal ulcer. In some embodiments, the CSA inhibits, reduces, or prevents pain.

In some embodiments, the therapeutic effect of the CSA is derived from its steroid-like structure. In other embodiments, the therapeutic effect of the CSA is derived from its antibiotic activity. In some embodiments, the therapeutic effect of the CSA is derived from a combination of antibiotic and anti-inflammatory activity. In other embodiments, the therapeutic effect of the CSA is derived from a combination of antibiotic and anti-pain activity. In some embodiments, the therapeutic effect of the CSA is derived from a combination of anti-inflammatory and anti-pain activity. In some embodiments, the therapeutic effect of the CSA is derived from a modulation of NFKB.

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt.

Co-Administration:

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers.

In some embodiments, one or more CSAs are co-administered. In other embodiments, the co-administration of CSAs accounts for their therapeutic benefit. In some embodiments, co-administration is concurrent.

In some embodiments, one or more CSAs having antibiotic activity are administered to the patient. In some embodiments, a single CSA is administered and responsible for both antibiotic activity and activity for treating any one or more of pain, gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, an autoimmune disorder, and/or a gastrointestinal ulcer, and/or pain associated with any of the aforementioned diseases. In some embodiments, the one or more CSAs having antibiotic activity are co-administered to the patient. In other embodiments, a non-CSA antibiotic is administered to the patient. In other embodiments, a non-CSA antibiotic is co-administered to the patient. Such agents include, but are not limited to, a regulatory agency approved antibiotic. In some embodiments, the regulatory agency is the Food and Drug Administration (FDA). In other embodiments, the antibiotic is an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, or a tetracycline.

In some embodiments, one or more non-CSA anti-inflammatory agents are administered to the patient. In some embodiments, the one or more non-CSA anti-inflammatory agents are co-administered. Such agents include, but are not limited to, a regulatory agency approved anti-inflammatory agent. In some embodiments, the regulatory agency is the Food and Drug Administration (FDA). In other embodiments, the anti-inflammatory agent is a non-steroidal anti-inflammatory agent ("NSAID") such as aspirin, diclofenac, ibuprogen, naproxen, rofecoxib, and the like. In some embodiments, acetaminophen is administered with the CSA. In other embodiments, the anti-inflammatory agent is a steroidal anti-inflammatory agent such as prednisone or prednisolone.

In some embodiments, the CSA is useful for treating pain associated with said disease state. Additional pain relievers are administered or co-administered to a patient in need thereof in certain embodiments. Such pain relievers include, but are not limited to, a regulatory agency approved pain reliever. In some embodiments, the regulatory agency is the Food and Drug Administration (FDA). Pain relievers are well known in the art and include the above mentioned NSAIDS and steroids, as well as acetaminophen, opioids, and the like.

Pharmaceutical Compositions

While it is possible for the compounds described herein to be administered alone, it may be preferable to formulate the compounds as pharmaceutical compositions (i.e., formulations). As such, in yet another aspect, pharmaceutical compositions useful in the methods and uses of the disclosed embodiments are provided. More particularly, the pharmaceutical compositions described herein may be useful, inter alia, for treating, reducing, or preventing a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer or a gastrointestinal ulcer, an autoimmune disorder, pain, and/or pain associated with said diseases. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein for the treatment of infection. In other embodiments, one or more CSAs are complexed with a protein for the treatment, reduction, or inhibition of a disease or symptom selected from gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer or a gastrointestinal ulcer, pain, and/or pain associated with said diseases. In some embodiments, one or more CSAs are complexed with a protein to increase the CSA's half-life. In other embodiments, one or more CSAs are complexed with a protein to decrease the CSA's toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA is about 18:1 or less, such as about 9:1 or less. In some embodiments, the CSA is coated with albumin.

Alternatively, or in addition, non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA is between about 8:1 and 1:1, preferably about 4:1. In some embodiments, the toxicity reducing compound is allantoin.

In some embodiments, a CSA composition is prepared utilizing one or more surfactants. In specific embodiments, the CSA is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In some embodiments, the one or more poloxamer surfactant in the composition has a molecular weight of about 3600 g/mol for the central hydrophobic chain of polyoxypropylene and has about 70% polyoxyethylene content. In some embodiments, the ratio of the one or more poloxamer to CSA is between about 50 to 1; about 40 to 1; about 30 to 1; about 20 to 1; about 10 to 1; about 5 to 1; about 1 to 1; about 1 to 10; about 1 to 20; about 1 to 30; about 1 to 40; or about 1 to 50. In other embodiments, the ratio of the one or more poloxamer to CSA is between 50 to 1; 40 to 1; 30 to 1; 20 to 1; 10 to 1; 5 to 1; 1 to 1; 1 to 10; 1 to 20; 1 to 30; 1 to 40; or 1 to 50. In some embodiments, the ratio of the one or more poloxamer to CSA is between about 50 to 1 to about 1 to 50. In other embodiments, the ratio of the one or more poloxamer to CSA is between about 30 to 1 to about 3 to 1. In some embodiments, the poloxamer is Pluronic F127.

The amount of poloxamer may be based upon a weight percentage of the composition. In some embodiments, the amount of poloxamer is about 10%, 15%, 20%, 25%, 30%, 35%, 40%, about any of the aforementioned numbers, or a range bounded by any two of the aforementioned numbers or the formulation. In some embodiments, the one or more poloxamer is between about 10% to about 40% by weight of a formulation administered to the patient. In some embodiments, the one or more poloxamer is between about 20% to about 30% by weight of the formulation. In some embodiments, the formulation contains less than about 50%, 40%, 30%, 20%, 10%, 5%, or 1% of CSA, or about any of the aforementioned numbers. In some embodiments, the formulation containes less than about 20% by weight of CSA.

The above described poloxamer formulations are particularly suited for the applications described herein, including the described methods of treatment, device coatings, preparation of unit dosage forms (i.e., solutions, mouthwashes, injectables), etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve an intended therapeutic effect.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with an osteogenesis agent or treatment or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

One of ordinary skill in the art to which these exemplary embodiments belong will understand that the compositions may be administered in numerous ways. In some exemplary embodiments, administration may be enteral, parenteral, or topical. Other exemplary routes of administration for contact or in vivo delivery which a compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and/or intralymphatic.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

In some embodiments, the composition or method includes administering a CSA from a pharmaceutically acceptable device(s) such as bandages, surgical dressings, gauzes, adhesive strips, surgical staples, clips, hemostats, intrauterine devices, sutures, trocars, catheters, tubes, and implants. In some embodiments, the implant is a pill, pellet, rod, screw, wafer, disc, and/or tablet. The devices can deliver the composition to a targeted area for a desired period of time. In some exemplary embodiments, the composition may be incorporated into a medical device coating. In some embodiments, the coating contains CSA as 0.1 weight %, 1 weight %, 5 weight %, 10 weight %, 15 weight %, 20 weight %, 25 weight %, 50 weight %, about any of the aforementioned numbers, and/or a range bounded by any two of the aforementioned numbers. In some embodiments, the thickness of the coating on the device depends on the desired elution profile and longevity of the device. Thicknesses may be about 1 nm, 50 nm, 100 nm, 500 nm, 1 μm, 10 μm, 50 μm, 100 μm, 250 μm, 500 μm, 750 μm, 1000 μm, a range bounded by any two of the aforementioned numbers, or at least about any of the aforementioned numbers, or less than about any of the aforementioned numbers.

Devices according to the disclosure can be prepared according to known methods, and can include, or be made from, polymeric material. In some instances, the polymeric material will be an absorbable material and in other instances, a non-absorbable material, or in other instances a resorbable material. Devices can, of course, include absorbable, non-absorbable, resorbable materials, and combinations thereof.

Absorbable materials can be synthetic materials and non-synthetic materials. Absorbable synthetic materials include, but are not limited to, cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. Absorbable non-synthetic materials include, but are not limited to, catgut, cargile membrane, fascia lata, gelatin, collagen, and combinations thereof.

Nonabsorbable synthetic materials include, but are not limited to nylons, rayons, polyesters, polyolefins, and combinations thereof. Non-absorbable non-synthetic materials include, but are not limited to, silk, dermal silk, cotton, linen, and combinations thereof.

Combinations of the foregoing devices and carriers/vehicles are also envisioned. For example, a CSA composition, gel, or ointment can be impregnated into a bandage or wound dressing for delivery of the CSA to a targeted location. As another example, an implantable absorbable device can be loaded with a CSA material and release the CSA from the device over a desired period. Sustained or controlled release formulations, compositions, or devices can be used. A desired period of delivery can be, for example, at least about 2, 3, 6, 10, 12, 18, or 24 hours, or 1, 2, 4, 8, 12, 20, or 30 days, or 1, 2, 3, 4, 5, 6, or more months, and any value in between. The physical form used to deliver the CSA is not critical and the choice or design of such devices is well within the level of skill of one in the art.

It may be desirable to provide for other conditions in the practice of the present methods. For example, it may be desirable to ensure that the target region is sufficiently oxygenated; generally, it is sufficient that atmospheric oxygen be present. It also may be desirable to maintain a desired level of moisture and a particular temperature; in some embodiments, a warm, moist environment is desirable. While not required, it may also be desirable to establish or maintain a sterile environment.

Additionally, it may be desirable to include other therapeutically beneficial agents in the formulation. For example, the vehicles or carriers may also include humectants or moisturizers to maintain a desired moisture level in the treated area. Other possibilities include drugs such as anesthetics or antibiotics, which provide other desired effects. Again, the possibilities are unlimited and are left to the practitioner. In some exemplary embodiments the composition may comprise a second CSA for purposes for which CSAs are known to serve.

Dosages

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, mouthwash, etc. which may include a composition in a freeze-dried or lyophilized state; a sterile liquid carrier, for example, can be added prior to administration or delivery in vivo. Unit dosage forms additionally include, for example, bottles, ampules, and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherwise locally delivered. Localized delivery is characterized by higher concentrations of drug at the site of desired action versus systemic concentrations of the drug. Well-known localized delivery forms can be used, including long-acting injections; infusion directly into the site of action; depot delivery forms; controlled or sustained delivery compositions; transdermal patches; infusion pumps; and the like. In some instances, the intended treatment area can be washed, rinsed, or inundated with a CSA composition. As a non-limiting example, the CSA composition is formulated as a mouthwash and the desired treatment area is an oral cavity, such as the mouth. In some embodiments, the CSA can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The systemic daily dosage regimen for an adult human patient may be, for example, an oral dose of between 0.01 mg and 3000 mg of the active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. Doses tailored for particular types of the diseases described herein, or for particular patients, can be selected based, in part, on the $GI_{50}$, TGI, and $LC_{50}$ values set forth in the Examples that follow.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 µg/mL, 0.1 µg/mL, 0.5 µg/mL, 1 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, 80 µg/mL, 85 µg/mL, 90 µg/mL, 95 µg/mL, 100 µg/mL, a range bounded by any two of the aforementioned numbers, or about any of the aforementioned numbers and ranges. In some embodiments, the therapeutic dose is sufficient to establish plasma levels in the range of about 0.1 µg/mL to about 10 µg/mL. In other embodiments, the therapeutic dose is sufficient to establish plasma levels in the range of 1 μg/mL to 20 μg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA is selected by measuring a biomarker in the patient. The term biomarker includes, but is not limited to, genetic regulation, protein levels, RNA levels, and cellular responses such as cytotoxicity. In some embodiments, one or more CSAs are selected by subjecting a sample from the patient to a companion diagnostic device. In some embodiments, the sample is a tissue sample. In other embodiments, the tissue sample is representative of the area to be treated. In some embodiments, the tissue sample contains a portion of the area to be treated. In some embodiments, the studied biomarker is a cellular response to the CSA or the companion diagnostic device measures a cellular response to the CSA. In some embodiments, the cellular response is a change in mRNA levels associated with inflammation.

EXAMPLES

Synthesis of CSAs

Compounds described herein can be prepared by known methods, such as those disclosed in U.S. Pat. No. 6,350,738, which are incorporated herein by reference. A skilled artisan will readily understand that minor variations of starting materials and reagents may be utilized to prepare known and novel cationic steroidal antimicrobials. For example, the preparation of CSA-13 disclosed in U.S. Pat. No. 6,350,738 (compound 133) can be used to prepare CSA-92 by using hexadecylamine rather than octyl amine as disclosed. Schematically, for example, the preparation of certain compounds can be accomplished as follows:

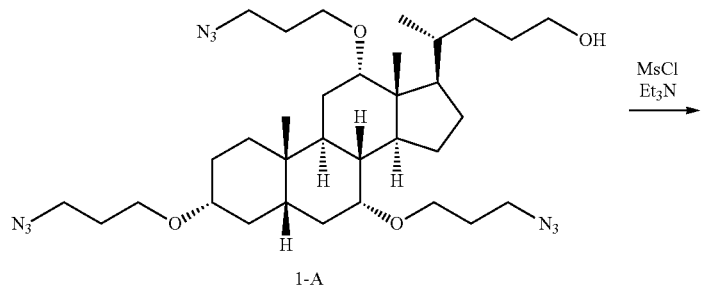

1-A

-continued

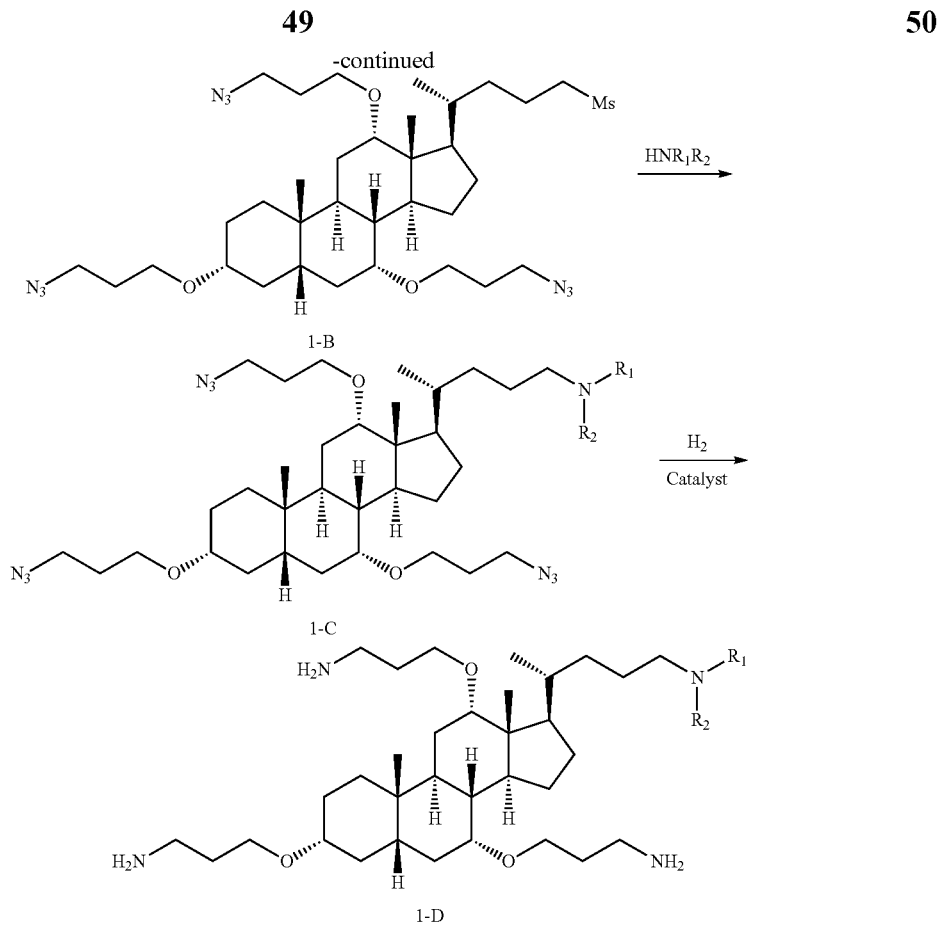

1-B

1-C

1-D

As shown above, compound 1-A is converted to the mesylate, compound 1-B using known conditions. Treatment of compound 1-B with a secondary amine, such as $HNR_1R_2$, results in the formation of compound 1-C, whose azido functional groups are reduced with hydrogen gas in the presence of a suitable catalyst to afford compound 1-D. Suitable catalysts include Palladium on Carbon and Lindlar catalyst. The reagent $HNR_1R_2$ is not particularly limited under this reaction scheme. For example, when $R_1$ is hydrogen and $R_2$ is a $C_8$-alkyl, CSA-13 is obtained from the synthesis. When $R_1$ is hydrogen and $R_2$ is a $C_{16}$-alkyl, CSA-92 is obtained from the synthesis. When $R_1$ and $R_2$ are both $C_5$-alkyl, CSA-90 is obtained from the synthesis.

Inflammation Gene Regulation

To determine the role of synthetic Ceragenins CSA-13, 44 and 90 in inflammation using mesenchymal stem cells (MSC), targeted mRNA panels from SABiosciences, and primary cells from Lonza were selected. Cells were purchased from Lonza.com and used fresh for each test using recommended media and culture conditions. After treatment, mRNA was isolated using Qiagen RNeasy Mini Kit®, and quantified using a NanoDrop 2000® by UV at 260 nm and 260/280 ratio for purity. cDNA was made using a First Strand Kit® from SABiosciences and processed for real time PCR using a kit from the same company for selected analysis of wound healing pathways. Results from q-PCR were uploaded to the SABiosciences site and to Ingenuity.com web site for analysis and pathway mapping. On day 1, primary human MSC cells were plated at 200,000 cells/well using E-well plates with 3 ml of recommended media— hMSC Basal Medium+BulletKit (50 ml Growth Supplement, 10 ml L-Glutamine and 0.5 ml Gentamicin Sulfate Amphotercin-B) for 24 hours. Only early passages of cells were used, and never from frozen stock. On day 2, cells were treated with compounds dissolved in DMSO diluted 1:1000 or more to avoid effects of the solvent. Final testing concentration for CSA-13 was 5.0 µM. Treatment lasted 8 hours, and was followed by RNA isolation using QIAGEN RNeasy Mini Kit® (74104). RNA was measured at 260/280 nm using a NanoDrop 2000® and normalized to 2.4 ng per well, cDNA preparation was done using QIAGEN First Strand kit 330401. q-PCR was run as absolute quantification and threshold set at 0.1 units. Dendritic cells were plated at 500,000 cells/well using 24-well plate with 500 µl of Lonza LGM-3 Complete Growth Medium with and without compound. Treatment lasted 8 hours, and was followed by RNA isolation using QIAGEN RNeasy Mini Kit® (74104). RNA was measured at 260/280 nm using NanoDrop2000® and normalized to 2.4 ng per well, cDNA preparation was done using QIAGEN First Strand kit 330401. PCR was run as absolute quantification and threshold set at 0.1 units. The results of these experiments are summarized in Tables 1-3 for CSA-13, 44, and 90, respectively. The results highlight the significant modulation of genes related to inflammation, such as IL1A (Interleukin-1 alpha), IL1B (Interleukin-1 beta), TLR2 (Toll-like receptor 2), TLR4 (Toll-like receptor 4), TLR6 (Toll-like receptor 6), TLR8 (Toll-like receptor 8), TLR9 (Toll-like receptor 9), TNF (Tumor necrosis factor), TNFRSF1A (Tumor necrosis factor receptor superfamily member 1A), IRAK2 (Interleukin-1 receptor-associated kinase 2), NFKB1 (Nuclear factor of kappa light polypeptide gene enhancer in B-cells 1), NFKB2 (Nuclear factor of kappa light polypeptide gene enhancer in B-cells 2), and NFKBIA (Nuclear factor of kappa light polypeptide gene enhancer in B-cells inhibitor, alpha). Such results clearly illustrate the potential of CSAs for modulating inflammation.

TABLE 1

Gene Expression Results for CSA-13

| Gene Symbol | Fold Regulation |
|---|---|
| IL1A | −5.5237 |
| IL1B | −16.3901 |
| TLR2 | −7.6418 |
| TLR4 | −2.6139 |
| TLR6 | −4.8417 |
| TLR8 | −2.107 |
| TLR9 | −2.1421 |
| TNF | −8.1805 |
| TNFRSF1A | −5.1031 |
| IRAK2 | −43.5175 |
| NFKB1 | −3.4437 |
| NFKB2 | −4.2155 |
| NFKBIA | −22.966 |

TABLE 2

Gene Expression Results for CSA-44

| Gene Symbol | Fold Regulation |
|---|---|
| IL1A | −6.0325 |
| IL1B | −28.5329 |
| IRAK2 | −31.8021 |
| NFKB1 | −3.2891 |
| NFKB2 | −2.2766 |
| NFKBIA | −52.206 |
| TLR2 | −15.7179 |
| TLR4 | −2.977 |
| TLR6 | −2.392 |
| TLR8 | −8.2256 |
| TLR9 | −1.8905 |
| TNF | −25.9588 |
| TNFRSF1A | −2.2461 |

TABLE 3

Gene Expression Results for CSA-90

| Gene Symbol | Fold Regulation |
|---|---|
| IL1A | −6.96 |
| IL1B | −3.6734 |
| IRAK2 | −52.0069 |
| NFKB1 | −4.718 |
| NFKB2 | −2.5474 |
| NFKBIA | −26.0352 |
| TLR2 | −13.6933 |
| TLR4 | −3.4278 |
| TLR6 | −2.0885 |
| TLR8 | −4.1972 |
| TLR9 | −1.8613 |
| TNF | −4.8514 |
| TNFRSF1A | −7.3196 |

Animal Model of Periodontitis:

CSA compounds and formulations are tested for the ability to eradicate infection by *P. gingivalis* and prevent alveolar bone loss in rat ligature model of periodontal disease. The rat ligature model is recognized as one of several models for evaluating the efficacy of topical formulations for treatment and/or prevention of periodontitis. Briefly, experimental periodontitis will be induced in 4 groups of 8 rats (sham treatment control, two treatment groups to evaluate two different CSA compounds and formulations, and one group of low dose of CSA compounds and formulation with the anti-inflammatory agent cimetidine) by placing silk sutures tied around the mandibular second premolars bilaterally, followed by the topical application of $10^9$ CFU of *P. gingivalis*. After 14 days treatment, the compounds and formulations are administered every other day continuing through day 42. The compounds and formulations are swabbed around the rat mouth and on the teeth. Volumes of 500 μL are used to ensure that sufficient material is present to coat the mouth and teeth. At the highest dose, this would be addition of 50 μg of CSA. In preliminary oral toxicity testing with rats, doses 1,000 times higher are well tolerated. Consequently, it is anticipated that toxicity will not be an issue.

At day 42 the study animals are euthanized. Mandibular block sections are obtained and tissues decalcified and embedded in paraffin. Thin sections (5 microns) are stained with hematoxylin and eosin. Macroscopic and histologic evaluation of the samples are conducted followed by characterization of cellular inflammatory infiltrate and quantitative histomorphometric measurements. Representative photographic images are also obtained. Alveolar bone loss is evaluated with the use of MicroCT scanning. Statistical analysis is also performed.

Alveolar bone loss associated with periodontitis is caused by inflammatory responses to bacterial infection and biofilm formation. As described above, deficiencies in antimicrobial peptides result in severe periodontitis. The endogenous antimicrobial peptide LL-37 displays antibacterial activity and anti-inflammatory activity. LL-37 sequesters bacterial membrane components, such as lipopolysaccharide and lipoteichoic acid that lead to inflammatory responses. Similarly, CSAs are expected to bind these bacterial lipids and thereby prevent inflammatory responses. This dual mode of action is expected to be very effective in limiting bacterial burden and in inhibiting inflammatory responses leading to alveolar bone loss. To separate these two effects, one series of experiments is performed with the anti-inflammatory cimetidine. Topical application of this compound was recently shown to reduce alveolar bone loss in a model of periodontal disease. Comparison of CSAs and CSA formulation (i.e., prepared with a surfactant such as pluronic), with and without cimetidine affords a method to evaluate the inflammatory properties of the test compounds and formulations in this model.

Animal Model of Pain/Inflammation:

Adult Male Sprague Dawley rats (200-250 g) are maintained on a 12/12 hour light/dark cycle with food and water ad libitum. Rats are acclimated for a week before use in experiments. Rats are anesthetized briefly with isoflurane (5% induction, then 2% maintenance) and their left foot is swabbed with ethanol. Complete Freund's adjuvant ("CFA") 0.15 mL is injected subcutaneously into the plantar surface of the left hind paw of the rat. The CFA injection immediately induces local inflammation, paw swelling, and pain. For behavior studies, rats are placed on the equipment and left to acclimate for 30 minutes. On day 0, baseline measurements are read and rats are injected with CFA thereafter. On day 3, post-CFA reads are taken and only rats that met criteria of hyperalgesia are placed on the study on day 4.

To assess mechanical allodynia, rats are placed on an elevated wire mesh platform, and to confine their movement, a 15×22×25 cm plexiglass chamber is placed over each animal. Mechanical paw withdrawal thresholds ("PWT") are measured by using a set of Semmes Weinstein monofilaments using the Dixon up and down method. Only rats that displayed a PWT of 8 g or less on day 3 (post-CFA) are placed on study. To assess thermal hyperalgesia rats are placed on glass plates with the source of heat applied from the bottom. On day 3 (post-CFA) rats that gave withdrawal latencies of 6 s or less are included in the experiments. Rats are then randomly assigned to either a vehicle group or drug group. On day 4, rats are treated with either the vehicle (saline), or drug (CSA, formulated CSA, or co-administration of CSA with anti-inflammatory and/or pain reliever) and reads are taken 2 hrs after the treatment. All drugs/vehicle are administered by oral gavage at 5 mg/kg/ml. Statistical analysis of behavioral data is performed using a one way ANOVA followed by the Student-Newman-Keul's Post-Hoc test.

Additional Animal Model of Pain

Application of a heat lamp to the hind paws of mice is used to determine sensitivity to painful thermal stimuli. During these tests the animals are awake and can behave freely within the confines of the cage. In the thermal sensitivity assay, the time it takes before the animal withdraws its paw from the heat source (hind paw withdrawal latency, HPWL) is taken as the measure of thermal sensitivity. To examine the influence of agents on nocifensive behavior, cumulative dose response relationships are tested, wherein an aliquot of CSA is administered every 60 minutes by i.p injection.

CONCLUSION

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of treating or reducing acute or chronic inflammation and/or pain associated with an inflammatory disease, comprising:
   identifying a patient in need of treating or reducing acute or chronic inflammation and/or pain associated with the inflammatory disease, which is selected from the group consisting of gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, a gastric ulcer, a peptic ulcer, a buccal ulcer, a nasopharyngeal ulcer, an esophageal ulcer, a duodenal ulcer, a gastrointestinal ulcer, and an autoimmune disorder; and
   administering a therapeutically effective amount of at least one cationic steroid antimicrobial (CSA) compound of Formula (III), or a pharmaceutically acceptable salt thereof, to the patient in need thereof, the therapeutically effective amount of the CSA compound treating or reducing acute or chronic inflammation and/or pain associated with the inflammatory disease by modulating gene expression via negative fold regulation of one or more genes related to inflammation selected from the group consisting of IL1A, IL1B, TLR2, TLR4, TLR6, TLR8, TLR9, TNF, TNFRSF1A, IRAK2, NFKB1, NFKB2, and NFKBIA, and thereby treating or reducing acute or chronic inflammation and/or pain independent of antimicrobial activity or microbial binding activity of the at least one CSA compound of Formula (III), wherein the at least one CSA compound of Formula (III) is:

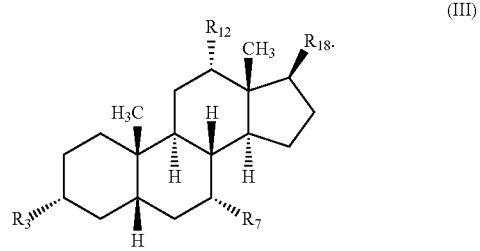

(III)

wherein:

$R_3$, $R_7$, and $R_{12}$ are independently selected from the group consisting of hydrogen, aminoalkyloxy and aminoalkylcarboxy, provided that at least two of $R_3$, $R_7$, and $R_{12}$ are independently selected from the group consisting of aminoalkyloxy and amino alkylcarboxy; and $R_{18}$ is selected from the group consisting of alkylaminoalkyl, alkoxycarbonylalkyl, alkylcarbonyloxyalkyl, di(alkyl)aminoalkyl, and alkylcarboxyalkyl, with the proviso that the CSA compound is not CSA-13.

2. The method of claim 1, wherein $R_3$, $R_7$, and $R_{12}$ are independently selected from the group consisting of hydrogen, substituted or unsubstituted $(C_1-C_{18})$ aminoalkyloxy and substituted or unsubstituted $(C_1-C_{18})$ aminoalkylcarboxy,; provided that at least two of $R_3$, $R_7$, and $R_{12}$ are independently selected from the group consisting of substituted or unsubstituted $(C_1-C_{18})$ aminoalkyloxy and substituted or unsubstituted $(C_1-C_{18})$ aminoalkylcarboxy; and $R_{18}$ is selected from the group consisting of substituted or unsubstituted $(C_1-C_{18})$ alkylamino $(C_1-C_{18})$ alkyl, substituted or unsubstituted di$(C_1-C_8$ alkyl)aminoalkyl, substituted or unsubstituted $(C_1-C_{18})$ alkylamino $(C_1-C_{18})$ alkyl, and substituted or unsubstituted $(C_1-C_{18})$ alkylcarboxy $(C_1-C_{18})$ alkyl.

3. The method of claim 1, wherein $R_3$, $R_7$, and $R_{12}$ are independently selected from the group consisting of hydrogen, unsubstituted $(C_1-C_{18})$ aminoalkyloxy and unsubstituted $(C_1-C_{18})$ aminoalkylcarboxy, provided that at least two of $R_3$, $R_7$, and $R_{12}$ are independently selected from the group consisting of unsubstituted $(C_1-C_{18})$ aminoalkyloxy and unsubstituted $(C_1-C_{18})$ aminoalkylcarboxy; and $R_{18}$ is selected from the group consisting of unsubstituted $(C_1-C_{18})$ alkylamino $(C_1-C_{18})$ alkyl, unsubstituted di$(C_1-C_{18}$ alkyl)aminoalkyl, unsubstituted $(C_1-C_{18})$ alkylamino $(C_1-C_{18})$ alkyl, and unsubstituted $(C_1-C_{18})$ alkylcarboxy $(C_1-C_{18})$ alkyl.

4. The method of claim 1, wherein the CSA, or a pharmaceutically acceptable salt thereof, is selected from the group consisting of:

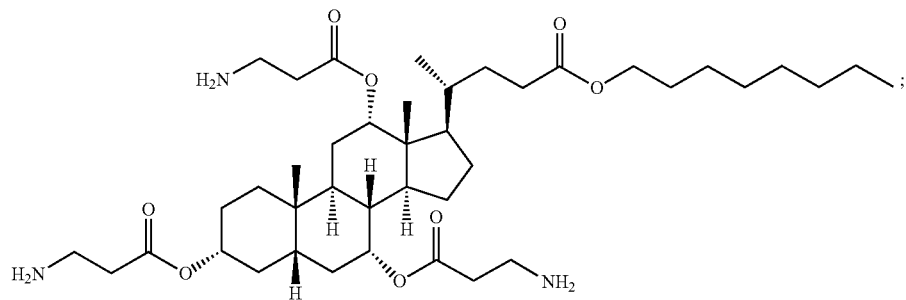
(CSA-44)
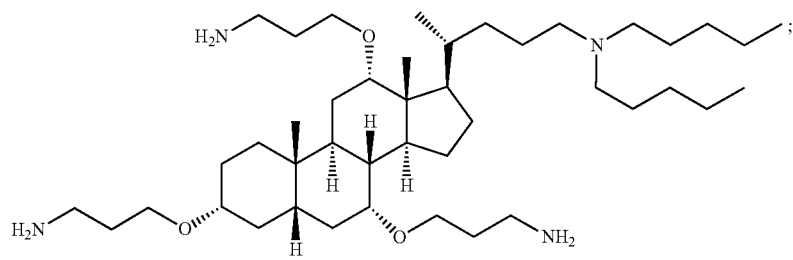
(CSA-90)
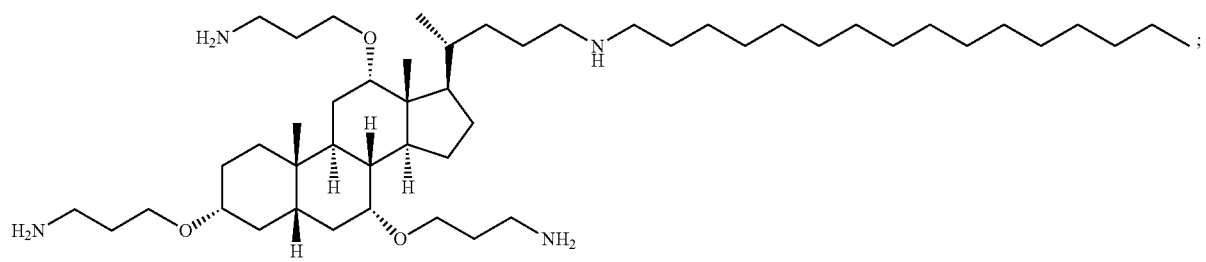
(CSA-92)
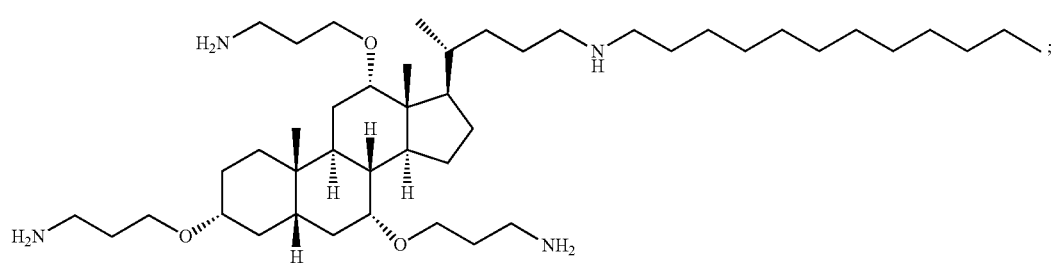
(CSA-131)
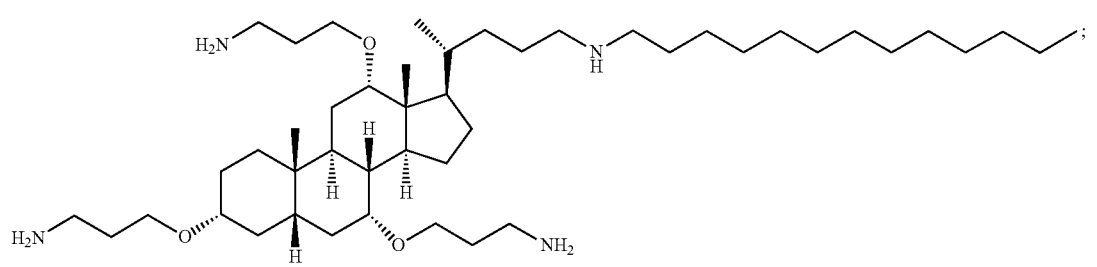
(CSA-138)

-continued

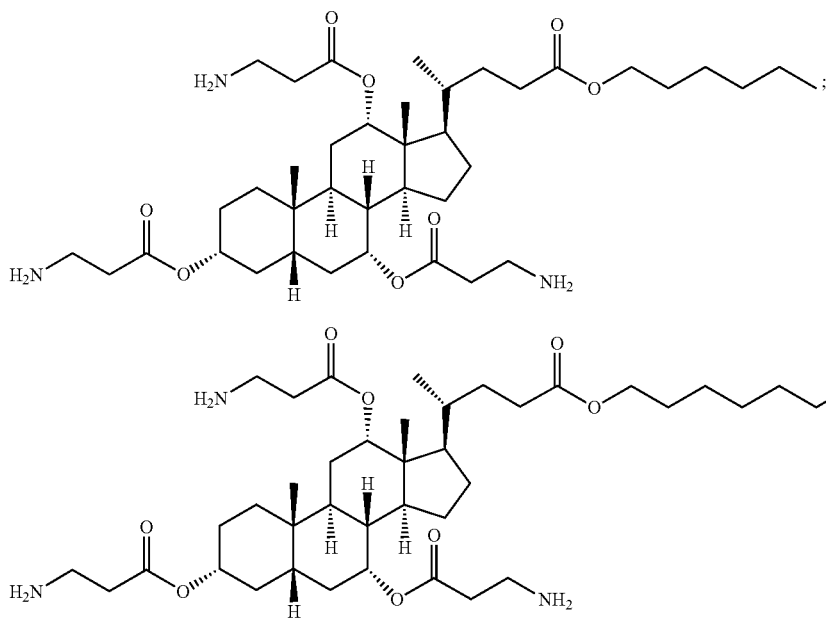

(CSA-142)

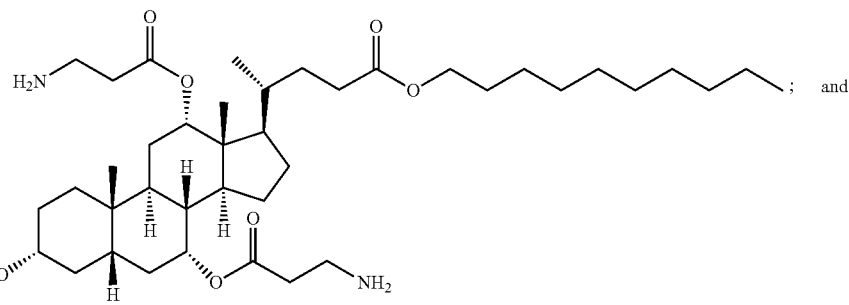

(CSA-144)

and pharmaceutically acceptable salts thereof.

5. The method of claim 1, wherein the pharmaceutically acceptable salt is a hydrochloride salt, mono-hydrochloride salt, a di-hydrochloride salt, a tri-hydrochloride salt, or a tetra-hydrochloride salt.

6. The method of claim 1, further comprising administering a non-CSA antibiotic to the patient.

7. The method of claim 6, wherein the antibiotic is selected from the group consisting of an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, and a tetracycline.

8. The method of claim 1, further comprising administering a non-CSA anti-inflammatory agent.

9. The method of claim 1, wherein the CSA inhibits resorption of the alveolar bone.

10. The method of claim 1, wherein the CSA inhibits inflammation.

11. The method of claim 1, wherein the CSA inhibits inflammation mediated by a tumor necrosis factor.

12. The method of claim 1, wherein the CSA is complexed with albumin.

13. The method of claim 1, wherein the CSA is complexed with one or more poloxamer surfactants.

14. The method of claim 13, wherein the ratio of the one or more poloxamer surfactants to CSA is between about 50:1 to about 1: 50.

15. The method of claim 13, wherein the ratio of the one or more poloxamer surfactants to CSA is between about 30:1 to about 3: 1.

16. The method of claim 13, wherein the one or more poloxamer surfactants are between about 10% to about 40% by weight of a formulation administered to the patient.

17. The method of claim 1, wherein the CSA is selected by measuring a biomarker or subjecting a sample from the patient to a companion diagnostic device in the patient.

18. The method of claim 17, wherein the biomarker is a cellular response to the CSA or the companion diagnostic device measures a cellular response to the CSA.

19. The method of claim 17, wherein the cellular response is a change in mRNA levels associated with inflammation.

20. The method of claim 1, wherein the disease is selected from gingivitis, buccal ulcer and periodontitis.

21. The method of claim 1, wherein the disease is selected from gastritis, colitis, ileitis, Crohn's disease, chronic inflammatory intestinal disease, inflammatory bowel syndrome, chronic inflammatory bowel disease, celiac disease, colitis, gastric ulcer, peptic ulcer, nasopharyngeal ulcer, esophageal ulcer, duodenal ulcer, and gastrointestinal ulcer.

22. The method of claim 1, wherein the disease is an autoimmune disorder.

23. The method of claim 1, wherein the patient is a mammal.

24. The method of claim 23, wherein the mammal is a human.

25. The method of claim 1, the therapeutically effective amount of the CSA compound effecting negative fold regulation of all of the one or more genes related to inflammation.

26. A method of treating or reducing acute or chronic inflammation and/or pain associated with an inflammatory disease', comprising:
    identifying a patient in need of treating or reducing acute or chronic inflammation and/or pain associated with the inflammatory disease, which is selected from the group consisting of gingivitis, periodontitis, gastritis, colitis, ileitis, Crohn's disease, chronic inflammatory intestinal disease, inflammatory bowel syndrome, chronic inflammatory bowel disease, celiac disease, ulcerative colitis, gastric ulcer, peptic ulcer, buccal ulcer, nasopharyngeal ulcer, esophageal ulcer, duodenal ulcer, gastrointestinal ulcer, and autoimmune disorder; and
    administering a therapeutically effective amount of at least one cationic steroid antimicrobial (CSA) compound, or a pharmaceutically acceptable salt thereof, to the patient in need thereof, the therapeutically effective amount of the CSA compound treating or reducing acute or chronic inflammation and/or pain associated with the inflammatory disease by modulating gene expression via negative fold regulation of one or more genes related to inflammation, and thereby treating or reducing acute or chronic inflammation and/or pain independent of antimicrobial activity or microbial binding activity of the at least one CSA compound, wherein the CSA compound or pharmaceutically acceptable salt thereof is selected from the group consisting of:

and/or pain associated with inflammatory bowel disease by modulating gene expression via negative fold regulation of one or more genes related to inflammation selected from the group consisting of IL1A, IL1B, TLR2, TLR4, TLR6, TLR8, TLR9, TNF, TNFRSF1A, IRAK2, NFKB 1, NFKB2, and NFKBIA, and thereby treating or reducing acute or chronic inflammation and/or pain associated with inflammatory bowel disease,

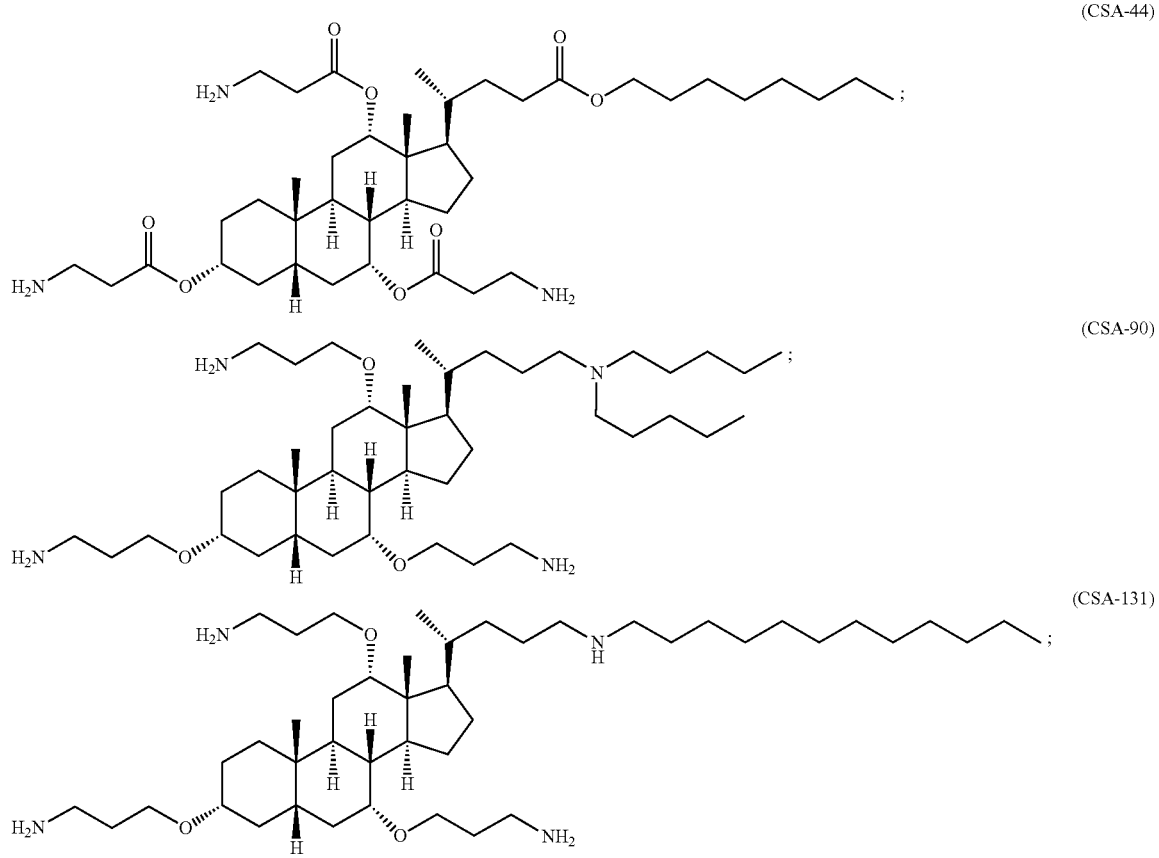

and pharmaceutically acceptable salts of the foregoing.

27. The method of claim 26, wherein the one or more genes related to inflammation are selected from the group consisting of IL1A, IL1B, TLR2, TLR4, TLR6, TLR8, TLR9, TNF, TNFRSF1A, IRAK2, NFKB1, NFKB2, and NFKBIA.

28. A method of treating or reducing acute or chronic inflammation and/or pain associated with inflammatory bowel disease, comprising:
 identifying a patient in need of treating or reducing acute or chronic inflammation and/or pain associated with inflammatory bowel disease; and
 administering a therapeutically effective amount of at least one cationic steroid antimicrobial (CSA) compound of Formula (III), or a pharmaceutically acceptable salt thereof, to the patient in need thereof, the therapeutically effective amount of the CSA compound treating or reducing acute or chronic inflammation wherein the at least one CSA compound of Formula (III) is:

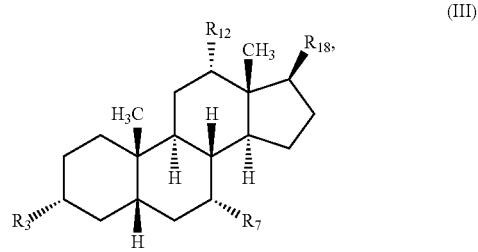

wherein:
 $R_3$, $R_7$, and $R_{12}$ are independently selected from the group consisting of hydrogen, aminoalkyloxy and aminoalkylcarboxy, provided that at least two of $R_3$, $R_7$, and $R_{12}$ are independently selected from the group consisting of aminoalkyloxy and amino-alkylcarboxy; and $R_{18}$ is selected from the group consisting of alkylaminoalkyl, alkoxycarbonylalkyl, alkylcarbonyloxyalkyl, di(alkyl)aminoalkyl, and alkylcarboxyalkyl, with the proviso that the CSA compound is not CSA-13.

29. The method of claim 28, the therapeutically effective amount of the CSA compound effecting negative fold regulation of all of the one or more genes related to inflammation.

* * * * *